(12) United States Patent
Schultz et al.

(10) Patent No.: US 12,012,483 B2
(45) Date of Patent: Jun. 18, 2024

(54) CROSS-LINKED RADIOPAQUE BIORESORBABLE POLYMERS AND DEVICES MADE THEREFROM

(71) Applicant: REVA MEDICAL, LLC, San Diego, CA (US)

(72) Inventors: Robert K. Schultz, Poway, CA (US); Lioubov Kabalnova, San Diego, CA (US); Donald K. Brandom, La Mesa, CA (US); Jessica Earley, San Diego, CA (US); Ernest G. Baluca, San Diego, CA (US); Durgadas Bolikal

(73) Assignee: Reva Medical, LLC, San Diego, CA (US)

( * ) Notice: Subject to any disclaimer, the term of this patent is extended or adjusted under 35 U.S.C. 154(b) by 808 days.

(21) Appl. No.: 17/265,663

(22) PCT Filed: Aug. 7, 2019

(86) PCT No.: PCT/US2019/045468
§ 371 (c)(1),
(2) Date: Feb. 3, 2021

(87) PCT Pub. No.: WO2020/033521
PCT Pub. Date: Feb. 13, 2020

(65) Prior Publication Data
US 2021/0380761 A1   Dec. 9, 2021

Related U.S. Application Data

(60) Provisional application No. 62/754,234, filed on Nov. 1, 2018, provisional application No. 62/715,928, filed on Aug. 8, 2018.

(51) Int. Cl.
C08G 64/18   (2006.01)
A61L 31/06   (2006.01)
(Continued)

(52) U.S. Cl.
CPC ............ *C08G 64/183* (2013.01); *A61L 31/06* (2013.01); *A61L 31/08* (2013.01); *A61L 31/148* (2013.01);
(Continued)

(58) Field of Classification Search
CPC ......... C08G 64/18; A61L 31/18; A61L 31/14; A61L 31/16; A61L 31/06; A61L 31/08;
(Continued)

(56) References Cited

U.S. PATENT DOCUMENTS

| | | | | |
|---|---|---|---|---|
| 5,899,917 A | * | 5/1999 | Edwards | A61L 31/18 |
| | | | | 606/195 |
| 2011/0190871 A1 | * | 8/2011 | Trollsas | A61F 2/82 |
| | | | | 623/1.15 |
| 2015/0359648 A1 | * | 12/2015 | Ma | A61L 31/06 |
| | | | | 623/1.38 |

FOREIGN PATENT DOCUMENTS

| | | | | | |
|---|---|---|---|---|---|
| EP | 2763712 | * | 5/2015 | ............ | A61L 31/04 |
| WO | WO 1999/024391 | | 5/1999 | | |

(Continued)

OTHER PUBLICATIONS

Shpaisman, N. et al., "One-Step Synthesis of Biodegradable Curcumin-Derived Hydrogels as Potential Soft Tissue Fillers after Breast Cancer Surgery", Biomacromolecules, 2012, vol. 13, pp. 2279-2286.

(Continued)

*Primary Examiner* — Walter E Webb
(74) *Attorney, Agent, or Firm* — Knobbe, Martens, Olson & Bear, LLP

(57) ABSTRACT

The present application provides polymer materials having the desired properties for implantation into a human or animal body, in particular, biocompatibility, biodegradability, radiopacity and mechanical properties. Methods of making such polymer materials, compositions or devices com- (Continued)

prising such polymer materials, and uses of such polymer materials, compositions and devices are also disclosed.

30 Claims, 6 Drawing Sheets

(51) Int. Cl.
  *A61L 31/08* (2006.01)
  *A61L 31/14* (2006.01)
  *A61L 31/16* (2006.01)
  *A61L 31/18* (2006.01)
  *C08J 3/24* (2006.01)

(52) U.S. Cl.
  CPC .............. *A61L 31/16* (2013.01); *A61L 31/18* (2013.01); *C08J 3/246* (2013.01); *A61L 2300/606* (2013.01); *A61L 2400/16* (2013.01); *A61L 2430/22* (2013.01); *C08G 2230/00* (2013.01); *C08G 2280/00* (2013.01); *C08J 2369/00* (2013.01)

(58) Field of Classification Search
  CPC ....... C08J 3/24; A61F 2/06; A61F 2/90; A61F 2/91; A61F 2/82
  USPC .......................................... 424/426; 606/195
  See application file for complete search history.

(56) References Cited

FOREIGN PATENT DOCUMENTS

| WO | WO 2005/030268 | 4/2005 |
|----|----------------|--------|
| WO | WO 2006/022754 | 3/2006 |
| WO | WO 2007/084444 | 7/2007 |
| WO | WO 2008/100346 | 8/2008 |
| WO | WO 2014/116716 | 7/2014 |

OTHER PUBLICATIONS

International Search Report issued in corresponding International Application No. PCT/US/2019/045468 dated Oct. 31, 2019.
International Preliminary Report on Patentability issued in corresponding Interntaional Application No. PCT/US/2019/045468 dated Feb. 9, 2021.
Extended European Search Report issued in corresponding EP Application No. 19847796.0, dated Apr. 8, 2022.

* cited by examiner

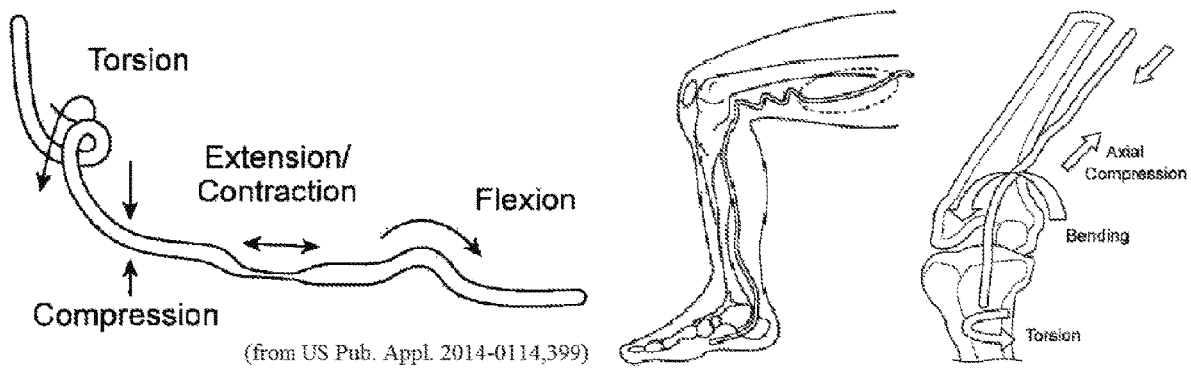
FIGURE 1
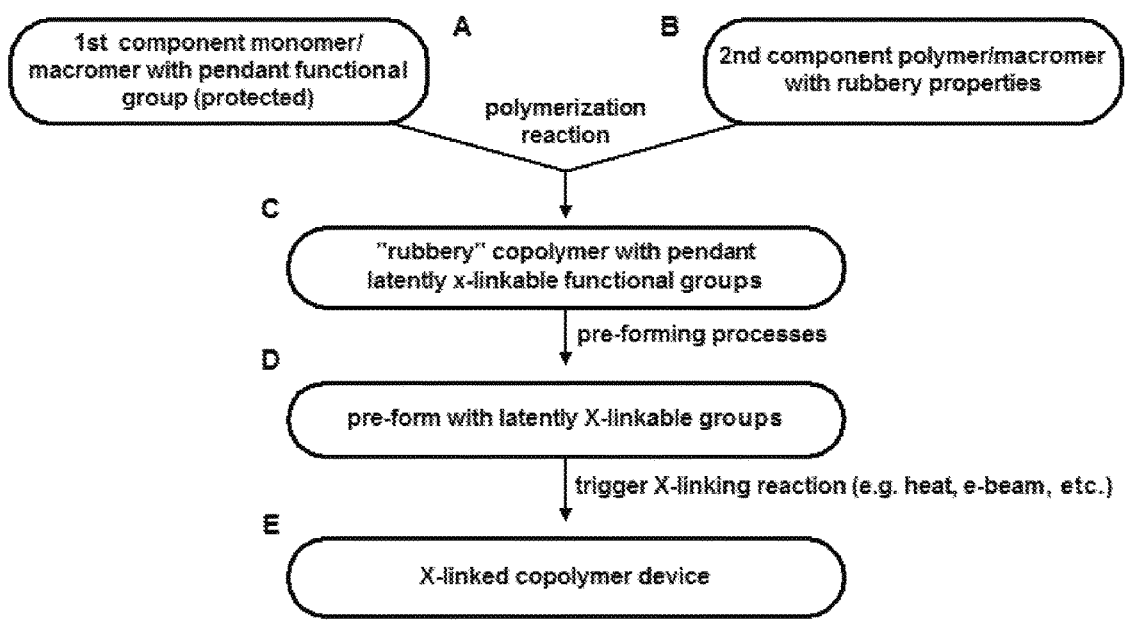
FIGURE 2 -- Scheme I - Cross-linkable pendent group on monomer

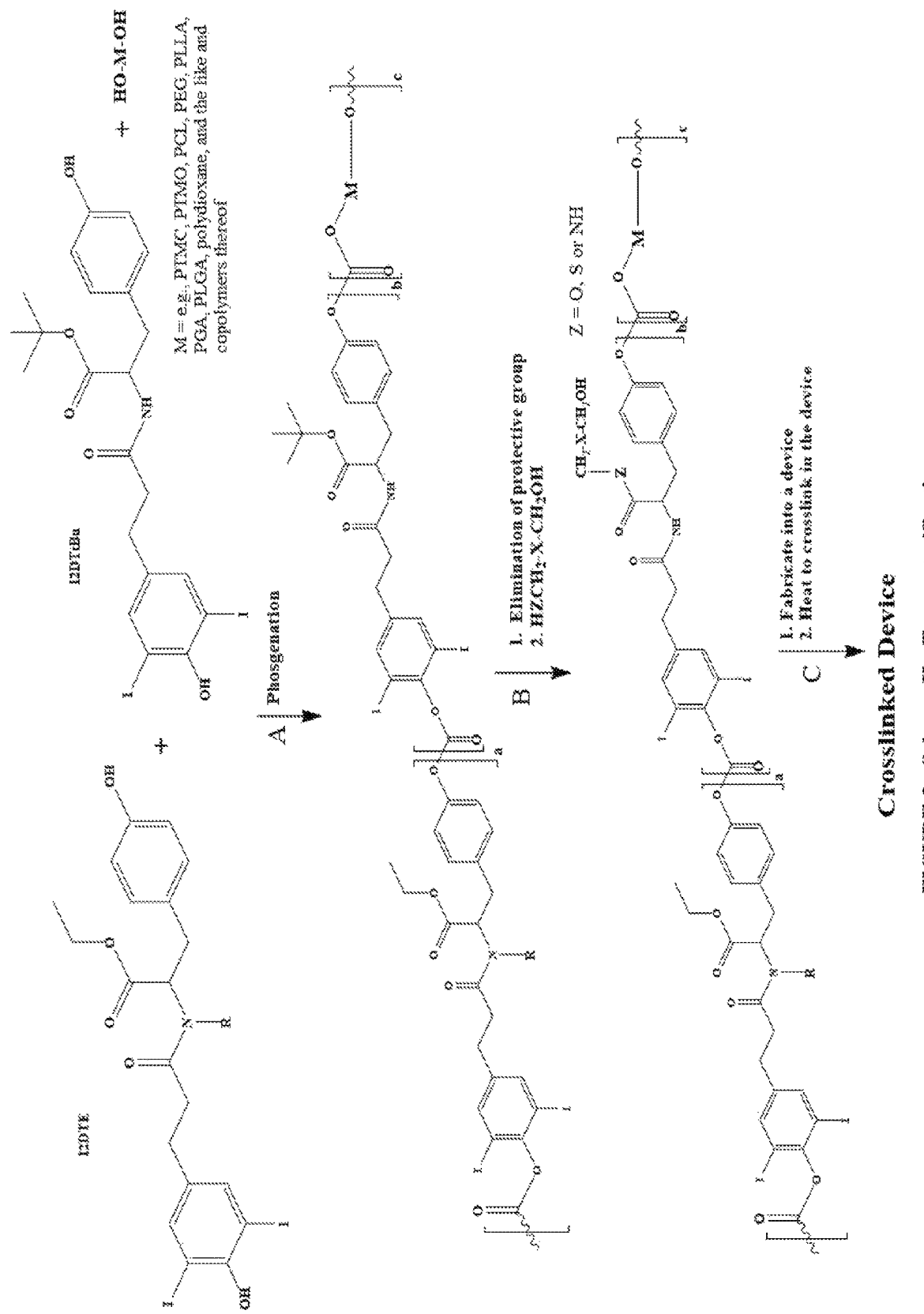
FIGURE 3 - Scheme II - Transesterification

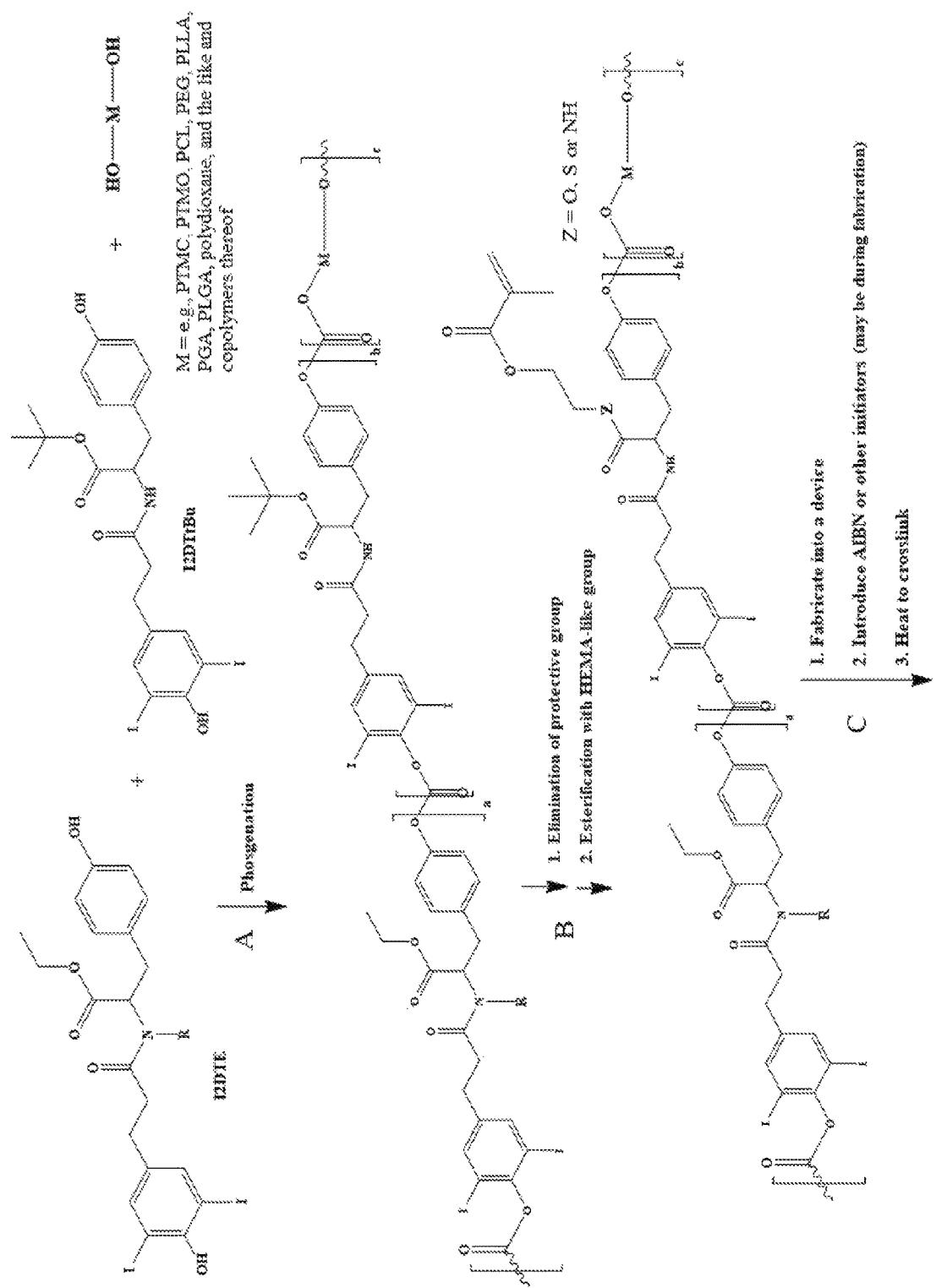
FIGURE 4 - Scheme III - Crosslinking via free radical addition

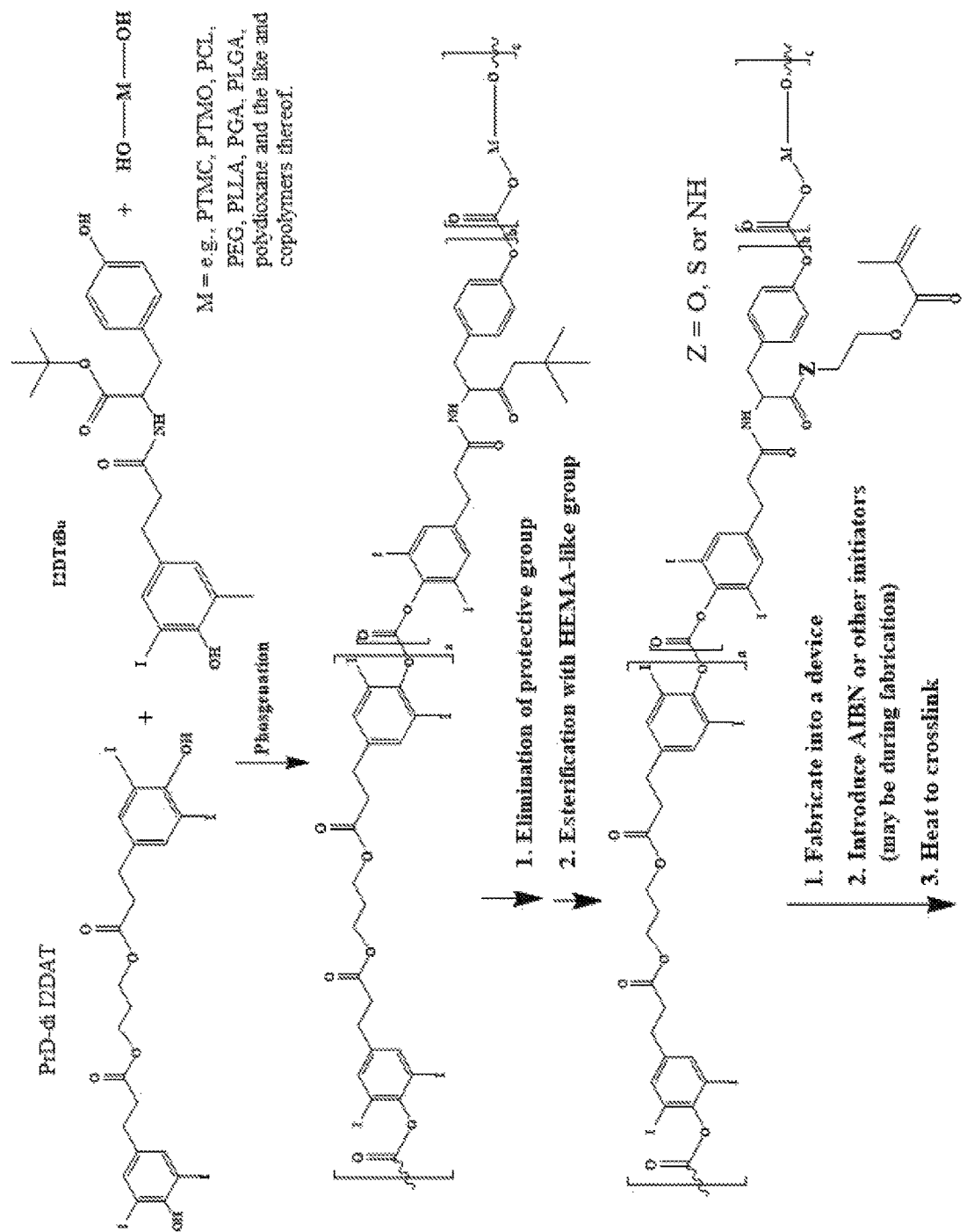
FIGURE 5 – Scheme IV – Cross-linking prepolymer comprising PrD-di I2DAT

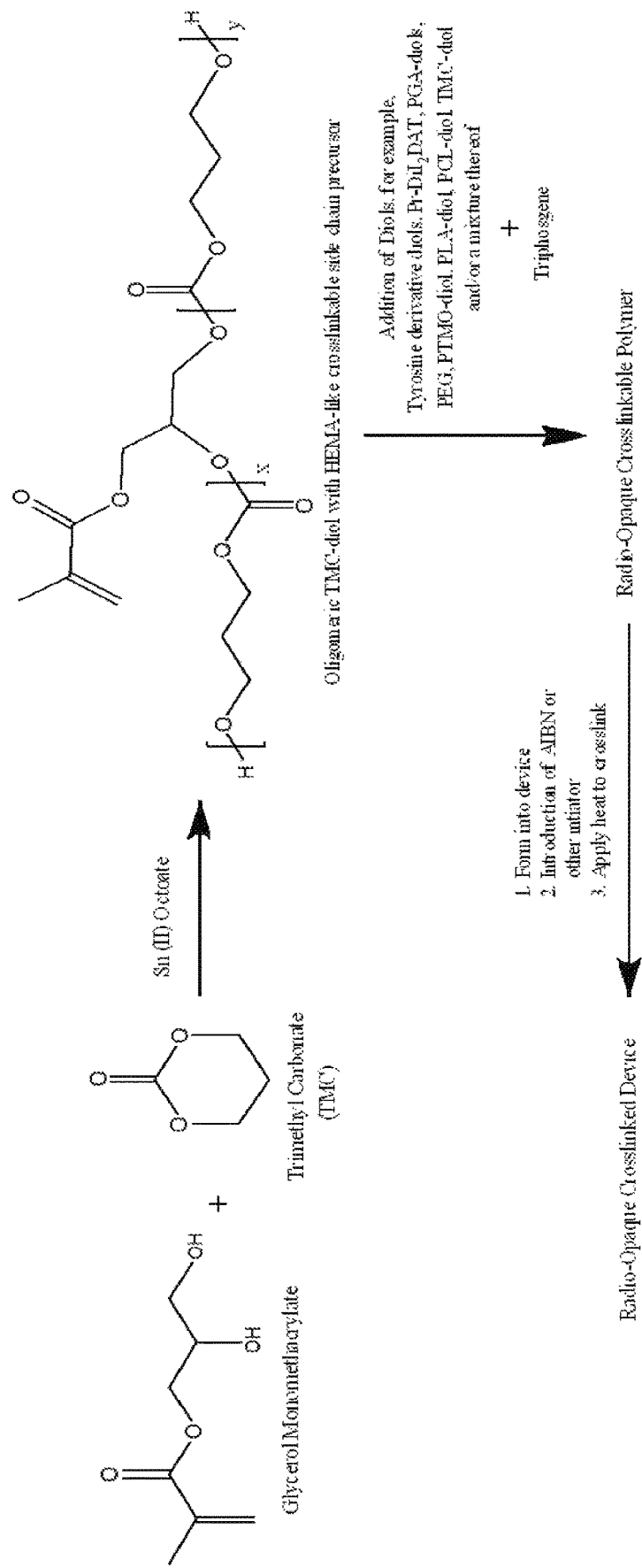
FIGURE 6 - Scheme V – Cross-linking prepolymer comprising TMC oligomers and HEMA-like functional groups

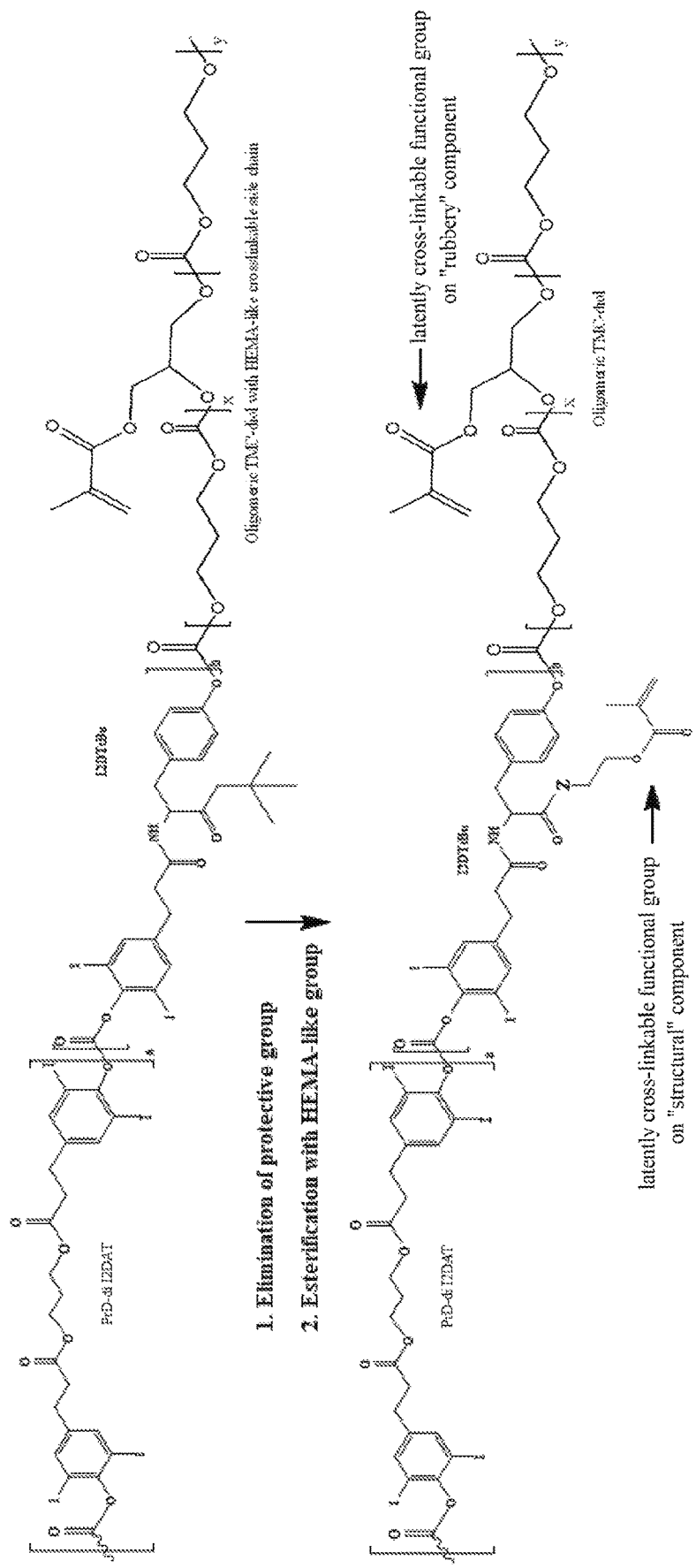
FIGURE 7 - Scheme VI – Polymer with multiple latently cross-linkable functional groups

CROSS-LINKED RADIOPAQUE BIORESORBABLE POLYMERS AND DEVICES MADE THEREFROM

INCORPORATION BY REFERENCE TO PRIORITY APPLICATIONS

The present application is a U.S. national stage application under 35 U.S.C. § 371 of PCT/US2019/045468, filed Aug. 7, 2019, which claims the benefit of priority to U.S. Provisional Application Nos. 62/715,928, filed Aug. 8, 2018, and 62/754,234, filed Nov. 1, 2018, all of which are hereby incorporated by reference in their entireties.

BACKGROUND

Field

The present inventions relate to methods, materials and devices for medical devices, and in particular medical devices for implantation within the body on a human or animal, and related materials and methods. Embodiments relate to materials that provide mechanical properties such as structural strength combined with toughness, resilience, crush-recoverability, and also such properties as biodegradability and radiopacity.

There are a number of areas of medical and therapeutic practice that have a need for devices, and in particular implantable devices, which have structures and materials which provide any or all of the following properties: high strength, high resilience and crush recoverability (the ability to return to original shape and size following mechanical deformation). In addition, the use of implantable devices within the body often creates the need for devices which are biocompatible, biodegradable and/or radiopaque. Among these areas of therapeutic practice employing implantable devices are interventions for diseases or conditions affecting body lumens, such as arteries, veins, various organ ducts, gastrointestinal, urinary, and the like. In addition, treatments in, or surrounding, joints require devices that are able to withstand the complex forces associated with these unique body areas.

For example, a particular area of therapeutic practice employing implantable devices includes vascular diseases. Vascular disease includes diseases of the arteries and veins (see e.g., https://en.wikipedia.org/wiki/Vascular_disease by Wikipedia contributors). A subcategory includes peripheral artery disease (PAD), which is associated with reduced flow in arteries in the circulation other than the heart or the brain.

In other examples, implantable devices may be employed for treatment in areas of the body that are characteristically subject to substantial movement. In such regions, such properties as fracture resistance and crush recovery may be required to prevent damage or changes to the structure of an implantable device due to patient activity. Applications may pertain to such areas as orthopedics and localized drug delivery.

In implantable medical devices of the prior art, it has been common to employ Nitinol or similar elastic or "shape memory" metallic alloys. For example, Nitinol stents have been used for treatment of peripheral vascular diseases, such as where an implant is required to restore and maintain patency in an artery or vein, particularly in regions subject to body movement. Another aspect of the prior art use of Nitinol is for self-expanding implant structures, such as self-expanding stents.

However, a salient limitation of Nitinol is that it is not biodegradable. Lack of biodegradability results in clinical limitations, among which is difficulty in retreatment in the region of the Nitinol stent and possible long term fatigue fracture of the devices leading to poor clinical outcomes.

Implantable devices also have been made from conventional biodegradable polymers, such as PLLA, and claims have been made for the crush recoverability of certain designs. However, such devices offer very limited fracture resistance, or to prevent fracture are designed with material formulations that are inherently weak. Additionally, such conventional biodegradable polymers are not radiopaque, and clinical applications generally required marker bands of heavy metals in order to achieve even marginal visibility under fluoroscopic examination.

There is a need for a material, as well as related devices and methods for implantation within the body, which has properties to cope with the high stress environment in portions of the body subject to tension, compression, bending and other like physical challenges, and which also possesses radiopacity and biodegradability. The mechanical challenges that need to be sustained in these applications require high scaffold performance in (a) extension/contraction, (b) compression, (c) flexion, (d) bending, and (e) torsion. FIG. 1 illustrates such physical challenges, using as an example the upper leg and knee region.

Additionally, various regions of the body are, either routinely or potentially, subject to substantial forces from impact or weight bearing.

The demand for high performance in such body regions requires devices which have high resilience to withstand the complex field of stresses. This spectrum of properties may include crush recoverability—the ability to re-expand and recover following a mechanical impact.

Likewise, there are important advantages to a device that is biodegradable in vivo, for example, to avoid complications due to permanent placement, and to allow the maximum opportunity for retreatment at the implant site at a later time. The device desirably provides an initial period of structural strength and integrity (e.g., approximately 1-6 months), followed by rapid degradation and elimination (e.g., within approximately 6-36 months).

In addition, materials and devices of the current invention may be radiopaque, permitting accurate fluoroscopic visualization during delivery and deployment.

SUMMARY

As set forth herein, the embodiments disclosed address the need for medical devices and materials having high strength, high resilience and/or crush recoverability, and particularly where embodiments of materials permit structures which are biocompatible, biodegradable and/or radiopaque. In particular examples, embodiments having aspects of the invention have properties that are suitable for use in challenging body environments subject to a high stress environment. Examples include implant devices for uses in anatomy or soft tissue subject to body motions. Implant devices that require properties of strength and toughness are applicable to treatment such as orthopedics, drug delivery, and the treatment of body lumens, such as arteries, veins, ducts, and the like.

Embodiments include of latently cross-linkable polymer material which may be pre-formed into shapes directed to the requirements of the desired medical device. Such pre-formed shapes may then be cross-linked by initialing cross-linkable polymer material. One result of carrying out such cross-linking reactions is the formation of a sufficient number or density of these cross-links within the material which enhances the properties so as to create a strong, tough elastic, and/or crush-recoverable material having the preformed shape. Optional subsequent processing may be employed to produce a final medical device.

In one purely illustrative non-limiting example, polymer materials having aspects of the invention may be employed in making scaffolds or other devices for restoring and/or maintaining patency or otherwise treating body lumens, such a such as arteries, veins, various organ ducts, gastrointestinal lumens, and the like. Embodiments may have high resilience and crush recoverability, and may include polymers which provide the strength needed for effective support for a vessel at a lesion site, followed by degradation and elimination permitting, among other things, retreatment of the vessel region. In addition, polymers and devices having aspects of the invention may be radiopaque, permitting accurate and convenient visualization by fluoroscopy during and subsequent to deployment.

Another illustrative example includes implants configured for controlled release of therapeutic formulations, including, the localized delivery of drugs and/or biologics. The polymer material embodiments of the invention are particularly suited to target regions where body movement may apply high stress to a delivery implant, creating risk of undesired disruption, movement and/or damage to the device. The resilience, strength and crush recoverability of the polymer material embodiments permit making delivery implants capable of resisting such impairment of function.

Such targeted implant delivery may include sustained release of a drug or other substance for a selected period of timed, release in a pre-selected profile, and/or in a sequential release of more than one drug or substance. The radiopacity of the polymer material embodiments supports accurate minimally invasive placement of such implants. Subsequent biodegradation can eliminate the residual material after the delivery function is complete.

A polymer material is disclosed herein. Various embodiments of the polymer material are described herein by utilizing a chemical formula or formulae to describe the material or a component thereof. Those skilled in the art will appreciate that such variables are generally defined consistently throughout the disclosure. Thus, in the event that the description of a particular embodiment does not expressly define a particular variable of such a chemical formula within the immediate context of that embodiment, those skilled in the art will understand that any description of that variable defined elsewhere herein can be applied to define that variable in the context of that embodiment. The polymer material comprises one or more of polymers, homogeneous polymers, copolymers, block co-polymers, and/or blends or mixtures thereof; wherein the biocompatible polymer material is optionally inherently radiopaque, and/or bioresorbable;

wherein the polymer material comprises at least one polymer component which, as initially prepared, has a latently cross-linkable state, such that it comprises functional groups which are configured to react upon being subjected to at least one cross-linking initiation treatment to crosslink the polymer;

wherein the polymer material comprises at least one polymer component which, as initially prepared, has a rubbery or partially rubber state at a temperature less than 37° C.;

wherein the polymer material, prior to being subjected to the at least one cross-linking initiation treatment, has properties allowing it to be formed into a selected structural shape without initiating cross-linking; and wherein the polymer material, after subjected to at least one cross-linking initiation treatment, has a cross-linked state, such that it has a sufficient number and/or density of cross-links between polymer chains within the material so as to enhance the material properties to create a strong, tough, resilient material, such that a selected shape composed of the cross-linked polymer material has crush-recoverable properties allowing substantial return to the selected shape following mechanical deformation.

In some embodiments of the polymer material of the preceding paragraph, the material is in a cross-linked state, the material having been subjected to the at least one initiation treatment. In some embodiments, the at least one polymer component which as initially prepared has a rubbery or partially rubber state, comprises one or more of PCL (polycaprolactone), PTMO (polytetramethylene oxide), PTMC (polytrimethylene carbonate), PEG (polyethylene glycol), polydioxanone, polyglycolide, polylactide, and any co-macromers thereof. In some embodiments, the at least one polymer component which has a latently cross-linkable polymer material comprises an inherently radiopaque, biocompatible, bioresorbable polymer, wherein the polymer comprises one or more of the recurring units having the following structure:

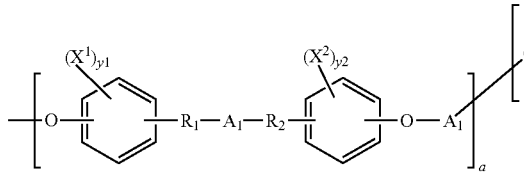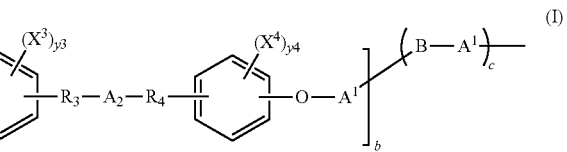

(I)

wherein each of "a," "b," "c", if the respective recurring unit is present, independently ranges between about 1% to about 5%, about 1% to about 10%, about 1% to about 15%, about 1% to about 20%, about 1% to about 25%, about 1% to about 30%, about 1% to about 35%, about 1% to about 40%, about 1% to about 45%, about 1% to about 50%, about 5% to about 10%, about 5% to about 15%, about 5% to about 20%, about 5% to about 25%, about 5% to about 30%, about 5% to about 35%, about 5% to about 40%, about 5% to about 45%, or about 5% to about 50% by weight of the polymer;

the polymer is a random or block co-polymer;

each of $X^1$, $X^2$, $X^3$ and $X^4$ is independently Br or I;

each of y1, y2, y3 and y4 is independently 0, 1, 2, 3 or 4;

a, b, and c are weight percentages range from 0 to 100% and a+b+c=100%; and $A_1$, $A_2$ and $A^1$ are linking groups independently selected from the group consisting of:

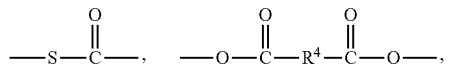

-continued

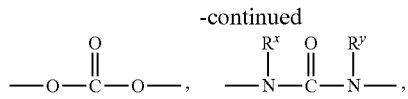

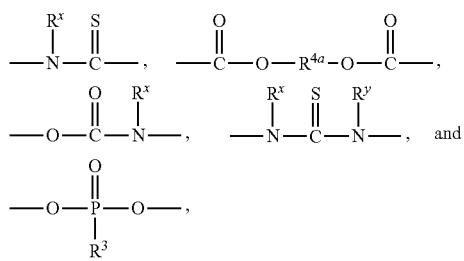

with the proviso that in the event an oxygen-oxygen or oxygen-nitrogen bond is implied by the linking of the $A_1$, $A_2$ or $A^1$ to a neighboring oxygen atom, then that neighboring oxygen atom is absent;

B is the at least one polymer component which as initially prepared has a rubbery or partially rubber state;

each of $R^x$, $R^y$, $R^3$ is independently H or $C_1$-$C_6$ alkyl;

each of $R^4$ and $R^{4a}$ is independently $C_1$-$C_{10}$ alkylene;

each of $R_1$, $R_2$, $R_3$ and $R_4$ is independently straight-chain or branched, saturated or unsaturated $C_1$-$C_{12}$ alkylene, 2-15 membered heteroalkylene, or 2-15 membered heteroalkenylene, each optionally comprising 1-3 heteroatoms each independently selected from O, NR, and S;

R is H or $C_1$-$C_6$ alkyl;

each of $R_1$, $R_2$, $R_3$ and $R_4$ optionally comprise a pendant Z group; and the pendant Z group optionally comprises functional groups that can react to crosslink the polymer, after it is fabricated into a desired shape, by either an elimination reaction or by a free radical mechanism.

In some embodiments, the polymer material comprises a polymer including one or more of the recurring units having the following structure:

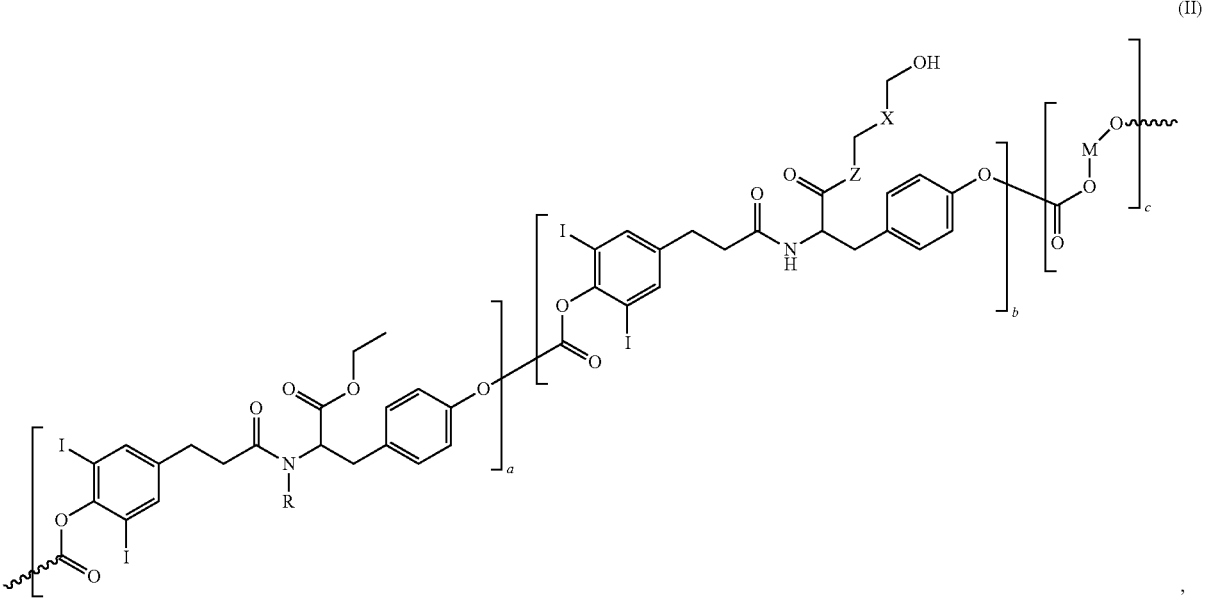

(II)

wherein:

M is a low Tg macromer, comprising PTMC, PTMO, PCL, PEG, or any co-macromers thereof, optionally further comprising one or more of PLLA, PGA, and polydioxane;

Z=O or NH; and

X is a bond or a straight chain or branched alkylene, alkenylene, or phenylene, each optionally substituted with one or more substituents selected from alkyl, halogen, —OH, and —C(O)OH; and the polymer is a random or block co-polymer;

wherein the at least one cross-linking initiation treatment comprises heating the latently cross-linkable polymer material to induce transesterification.

In some embodiments, the polymer material comprises a polymer including one or more of the recurring units having the following structure:

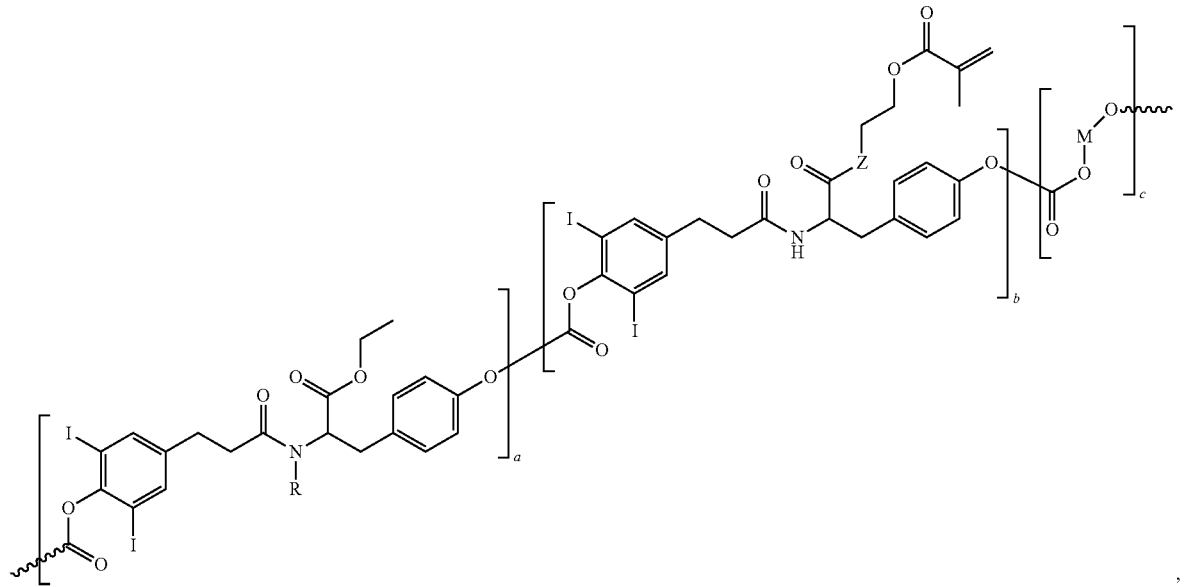

wherein:
M is a low Tg macromer, comprising PTMC, PTMO, PCL, PEG, or any co-macromers thereof, optionally further comprising one or more of PLLA, PGA, and polydioxane; and
Z=O or NH; and
the polymer is a random or block co-polymer;

wherein the at least one cross-linking initiation treatment comprises a free radical initiated chain reaction of polymer in the presence of free radical initiator.

In some embodiments, the polymer material comprises a polymer including one or more of the recurring units having the following structure:

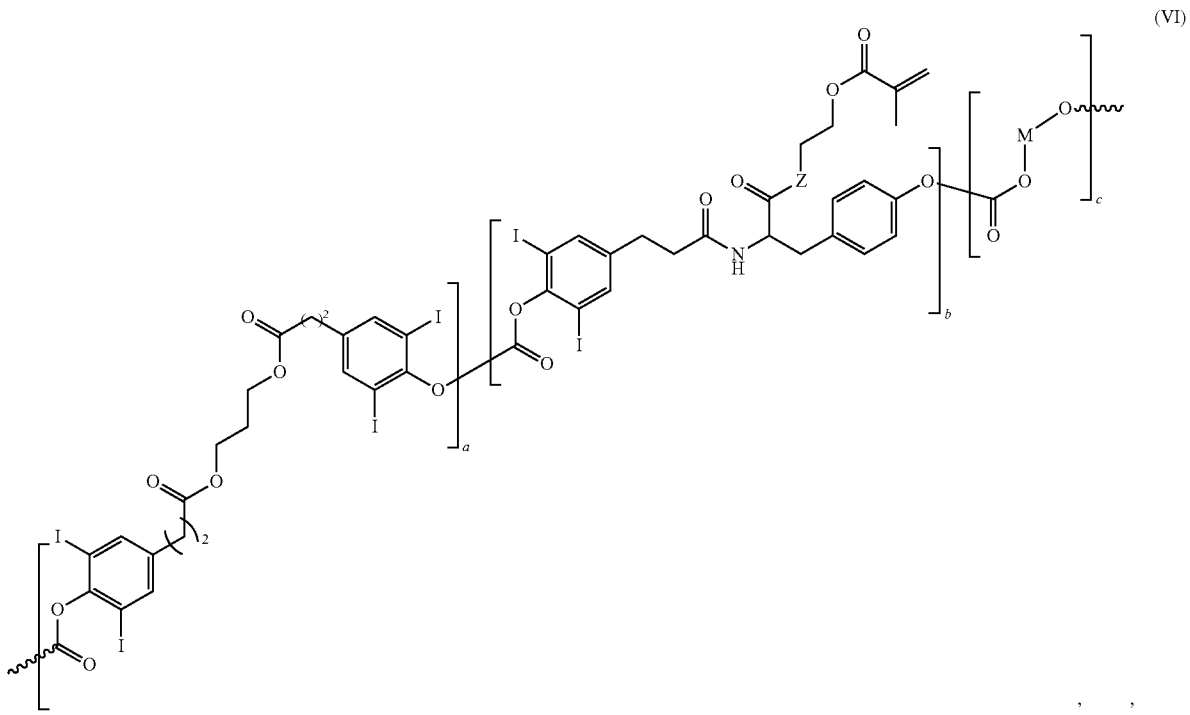

wherein
  M is a low Tg macromer, comprising PTMC, PTMO, PCL, PEG, or any co-macromers thereof, optionally further comprising one or more of PLLA, PGA, and polydioxane; and
  Z=O or NH; and
  wherein the at least one cross-linking initiation treatment comprises a free radical initiated chain reaction of polymer in the presence of free radical initiator.

In some embodiments, the moiety in brackets "b" is replaced by a t-butyl ester of diphenolic acid according to the following structures:

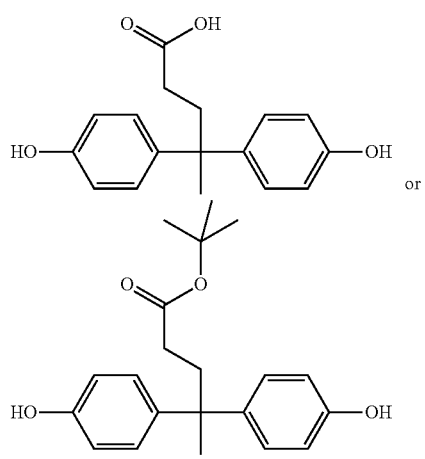

or

In some embodiments of the polymer material, R=H. In some embodiments, R is a straight chain or branched chain alkyl group. In some embodiments, R is $CH_3$ or $C_2H_5$.

In some embodiments, the polymer material comprises a polymer including one or more of the recurring units having the following structure, when crosslinking functional group is in the side chain of an inherently rubbery PTMC:

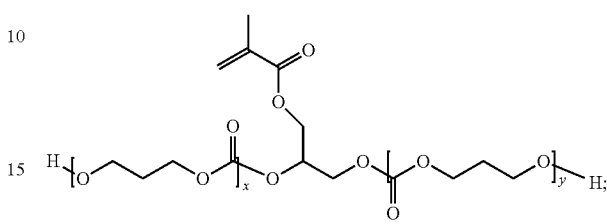

wherein each of x and y is independently an integer in the range of about 1 to about 50

In some embodiments, the polymer material comprises a polymer including at least two distinct kinds of the recurring units, each such kind of recurring unit having a different type of the latently crosslinkable functional groups; and
  wherein one such recurring unit is a structural radiopaque component including a crosslinkable acryloyl or methacryloyl moiety in the pendant group; and
  wherein another such recurring unit is an inherently rubbery component including a crosslinkable acryloyl or methacryloyl moiety in the pendant group.

In some embodiments, the polymer material comprises a polymer including one or more of the recurring units having the following structure:

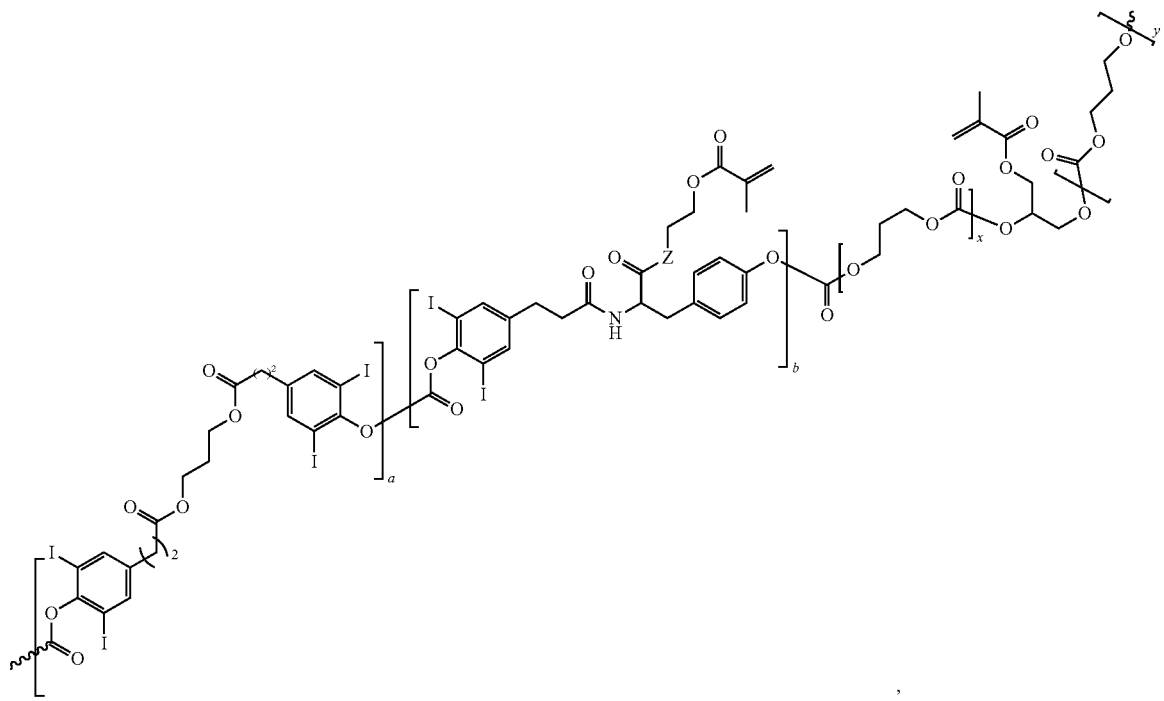

wherein Z is O, S or NH.

A medical device is also disclosed herein. The medical device comprises at least one structural portion;
  wherein the structural portion has been previously formed from a latently cross-linkable polymer material to have a pre-formed shape, the latently cross-linkable polymer material including one or more polymers or copolymers which are inherently radiopaque, biocompatible, and/or bioresorbable.
  wherein, subsequent to the formation of the pre-formed shape of the structural portion, the latently cross-linkable polymer material of the structural portion has been subjected to at least one cross-linking initiation treatment so as to form a sufficient number and/or density of cross-links between polymer chains within the material so as to enhance the material properties to create a strong, tough, resilient, and/or crush-recoverable material having the pre-formed shape; and
  wherein optionally the cross-linked pre-form shape is further fabricated to make the medical device.

In some embodiments of a medical device as described herein, the latently cross-linkable polymer material comprises an inherently radiopaque, biocompatible, bioresorbable polymer, wherein the polymer comprises one or more of the recurring units having the following structure:

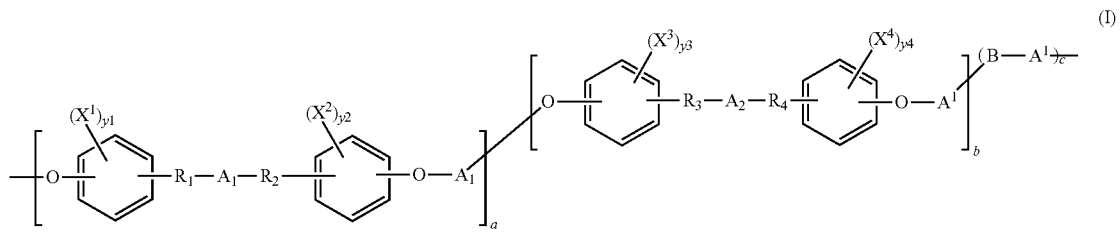

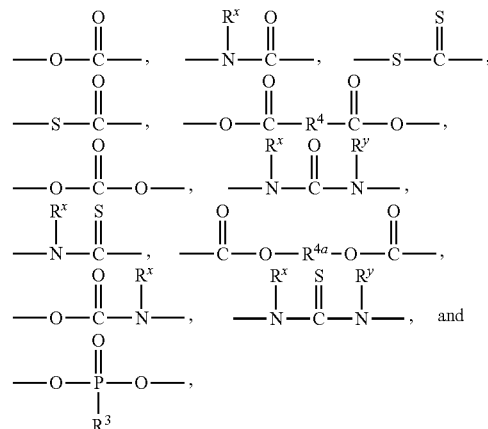

with the proviso that in the event an oxygen-oxygen or oxygen-nitrogen bond is implied by the linking of the $A_1$, $A_2$ or $A^1$ to a neighboring oxygen atom, then that neighboring oxygen atom is absent;

B is the at least one polymer component which as initially prepared has a rubbery or partially rubbery state;

each of $R^x$, $R^y$, $R^3$ is independently H or $C_1$-$C_6$ alkyl;

each of $R^4$ and $R^{4a}$ is independently $C_1$-$C_{10}$ alkylene;

wherein
  each of "a," "b," "c", if the respective recurring unit is present, independently ranges between about 1% to about 5%, about 1% to about 10%, about 1% to about 15%, about 1% to about 20%, about 1% to about 25%, about 1% to about 30%, about 1% to about 35%, about 1% to about 40%, about 1% to about 45%, about 1% to about 50%, about 5% to about 10%, about 5% to about 15%, about 5% to about 20%, about 5% to about 25%, about 5% to about 30%, about 5% to about 35%, about 5% to about 40%, about 5% to about 45%, or about 5% to about 50% by weight of the polymer;
  the polymer is a random or block co-polymer;
  each of $X^1$, $X^2$, $X^3$ and $X^4$ is independently Br or I;
  each of y1, y2, y3 and y4 is independently 0, 1, 2, 3, or 4;
  a, b, and c are weight percentages range from 0 to 100% and a+b+c=100%; $A_1$, $A_2$ and $A^1$ are linking groups independently selected from each of $R_1$, $R_2$, $R_3$ and $R_4$ is independently a straight-chain or branched, saturated or unsaturated $C_1$-$C_{12}$ alkylene, 2-15 membered heteroalkylene, or 2-15 membered hetero-($C_1$-$C_{12}$)alkenylene, each optionally comprising 1-3 heteroatoms each independently selected from O, NR, and S;

R is H or $C_1$-$C_6$ alkyl, each of $R_1$, $R_2$, $R_3$ and $R_4$ optionally comprising a pendant Z group and;

the pendant Z group optionally comprises functional groups that can react to crosslink the polymer, after it is fabricated into a desired shape, by either an elimination reaction or by a free radical mechanism.

In some embodiments of a medical device as described herein, the latently cross-linkable polymer material comprises the following structure:

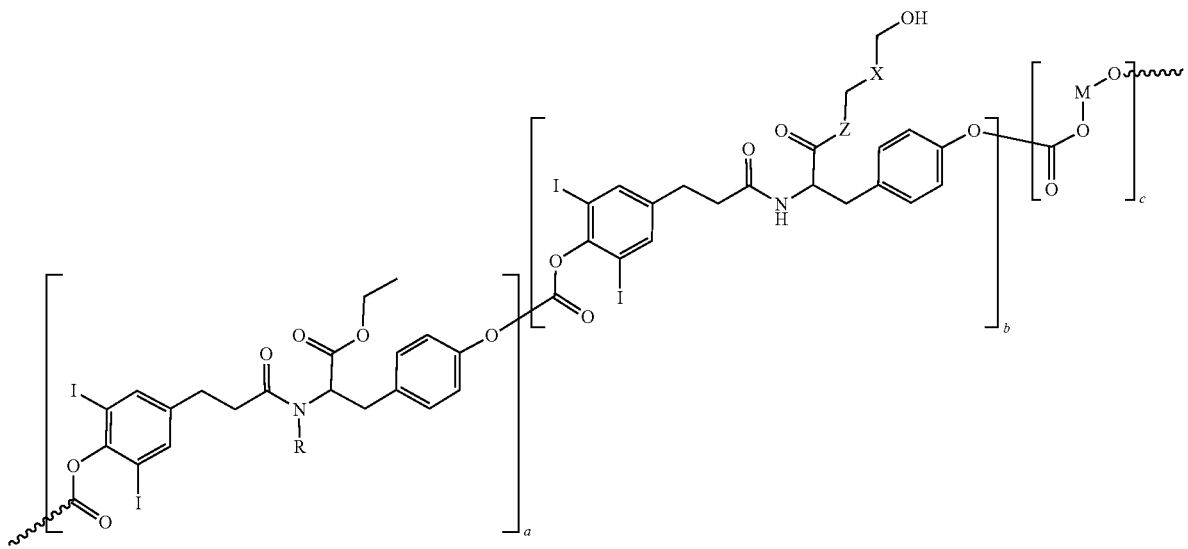

(II)

wherein
M comprises a low Tg macromer, further comprising PTMC, PTMO, PCL, PEG, PLLA, PGA, polydioxane, or any co-macromers thereof;
Z=O or NH; and
X is a straight chain or branched alkylene, alkenylene, or substituted or unsubstituted phenylene, wherein the at least one cross-linking initiation treatment comprises heating the latently cross-linkable polymer material to induce transesterification.

In some embodiments of a medical device as described herein, the latently cross-linkable polymer material comprises the following structure:

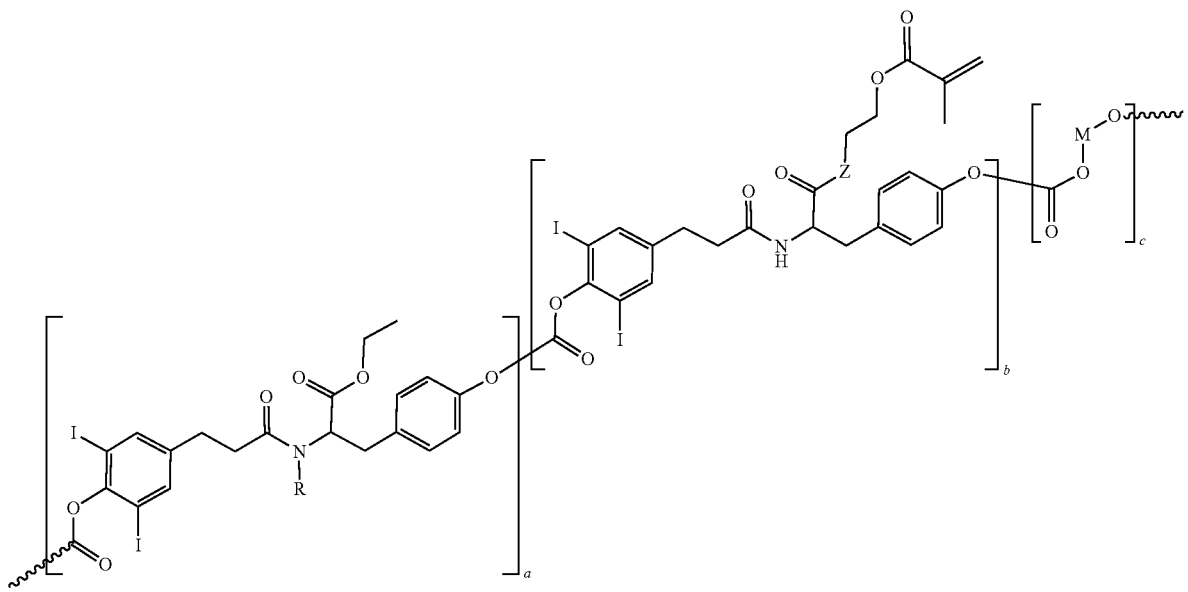

(III)

wherein
M comprises a low Tg macromer, further comprising PTMC, PTMO, PCL, PLLA, PGA, polydioxane, or any co-macromers thereof; and
Z=O or NH; and wherein the at least one cross-linking initiation treatment comprises a free radical initiated chain reaction of polymer in the presence of free radical initiator.

In some embodiments of a medical device as described herein, the latently cross-linkable polymer material comprises the following structure:

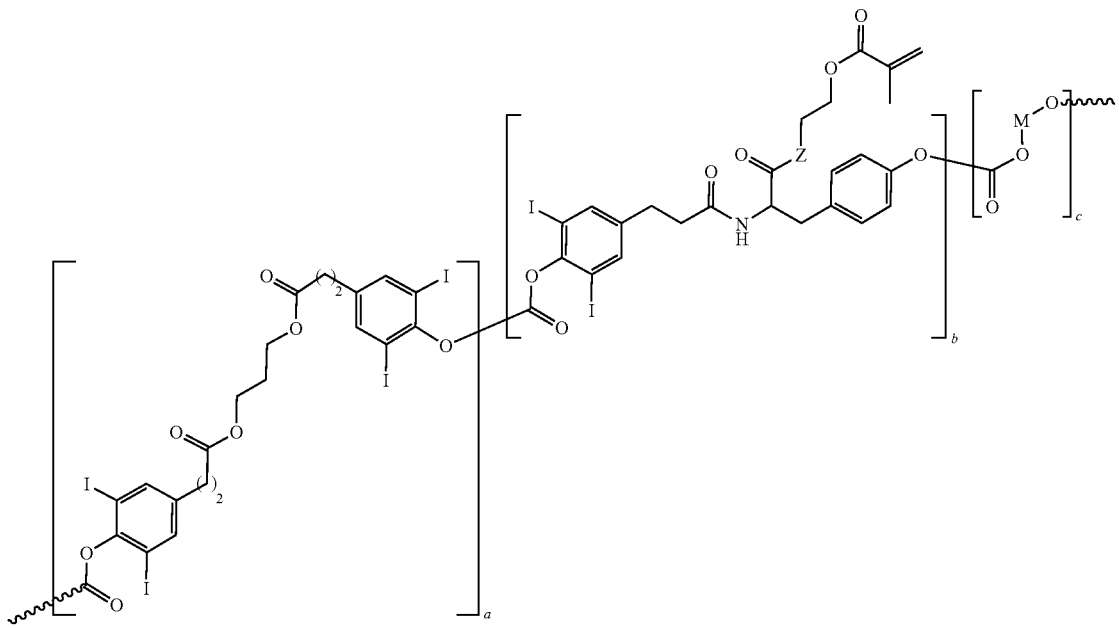

In some embodiments of a medical device as described herein, the pre-formed shape of the structural portion is tubular. In some embodiments, the tubular pre-formed shape of the structural portion is laser-cut to form at least a portion of a vascular scaffold device, the laser cutting being either prior to or subsequent to cross-linking of the polymer material.

A method of making a medical device is also provided herein. The medical device has a structure comprising an inherently radiopaque, biocompatible, and/or bioresorbable polymeric material, the structure having at least one of the properties of toughness, resiliency, impact-resistance and/or crush recoverability upon deformation, the method comprising, in any functional order, the steps of:
  (a) preparing a latently cross-linkable polymer material which comprises polymer or copolymer which is inherently radiopaque, biocompatible and/or bioresorbable, and which is capable of subsequently forming cross-links between polymer chains upon being subjected to at least one cross-linking initiation treatment;
  (b) forming at least one pre-formed structural shape portion, the pre-formed structural shape portion including the latently cross-linkable polymer material;
  (c) after forming step (b), subjecting the pre-formed structural shape portion to at least one cross-linking initiation treatment so as to forming cross-links between polymer chains, resulting in the formation of a cross-linked structural shape portion having at least one of the properties of toughness, resiliency, impact-resistance and/or crush recoverability upon deformation;
  (d) after treatment step (c), optionally carrying out forming, treating and/or conditioning steps to modify the cross-linked structural shape portion; and
  (e) making the medical device so as to comprise the cross-linked structural shape portion.

In some embodiments, a medical device is made using all or a portion of the steps, in any order, of a method as disclosed herein.

In some embodiments, the device comprises a vascular scaffold.

In some embodiments, the medical device comprises a polymer including one or more of the recurring units having the following structure:

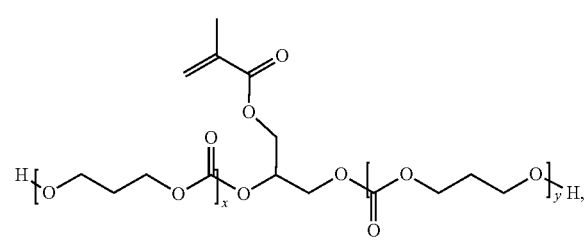

wherein:
  each of x and y is independently an integer in the range of about 1 to about 50.

In some embodiments, the device comprises a polymer including one or more of the recurring units having the following structure:

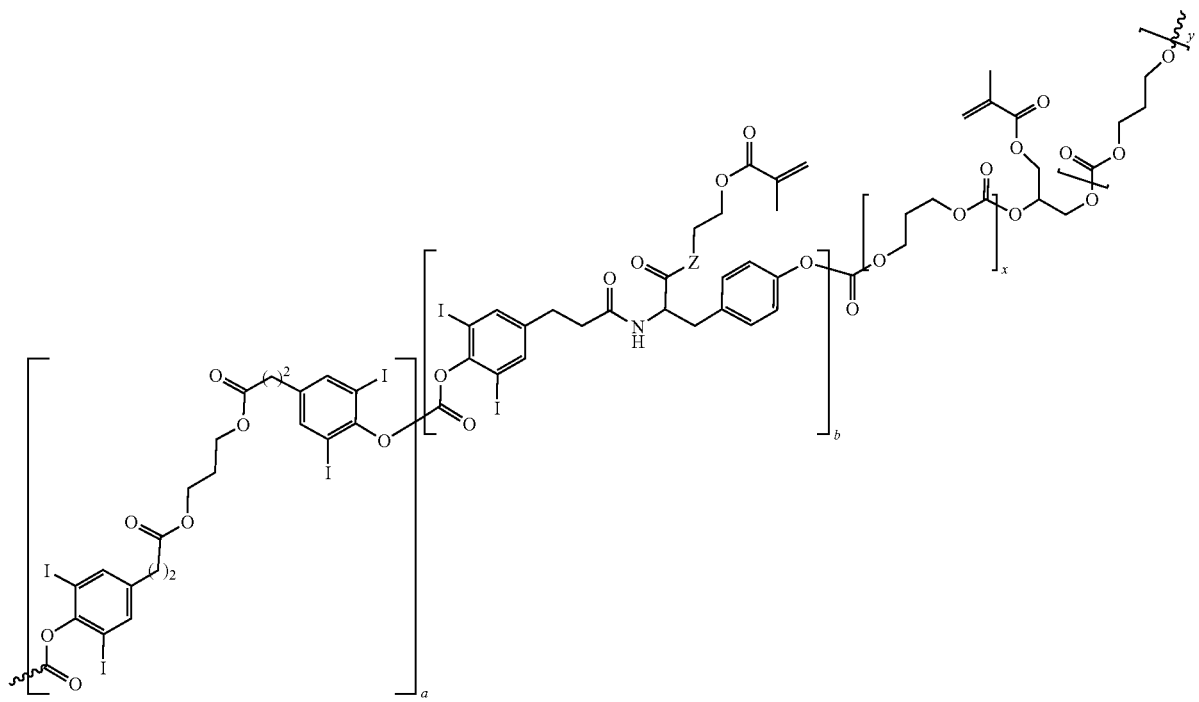

wherein Z is O, S or NH.

In some embodiments, the medical device comprises a coating including a drug and/or pharmaceutic agent. The aforementioned and other embodiments are described in greater detail below.

BRIEF DESCRIPTION OF THE DRAWINGS

The abovementioned and other features of the embodiments disclosed herein are described below with reference to the drawings of the embodiments. The illustrated embodiments are intended to illustrate, but not to limit the embodiments. The drawings contain the following figures:

FIG. 1 depicts various mechanical challenges experienced by certain body regions due to body movement, as exemplified by the leg and knee region.

FIG. 2 is a flow chart outlining an exemplary approach to making a medical device having aspects of the invention (Scheme I)

FIG. 3 illustrates one example of a reaction scheme for preparing latently crosslinkable polymers via transesterification (Scheme II).

FIG. 4 illustrates one example of a reaction scheme for preparing latently crosslinkable polymers via free radical polymerization (Scheme III).

FIG. 5 illustrates another example of a reaction scheme for preparing latently crosslinkable polymers via free radical polymerization (Scheme IV).

FIG. 6 illustrates a reaction scheme for preparing latently crosslinkable polymers via free radical polymerization using trimethylene carbonate oligomeric diols with HEMA-like double bonds in side chains (Scheme V).

FIG. 7 illustrates a reaction scheme for preparing latently crosslinkable polymers wherein there are multiple distinct types of latently cross-linkable functional groups (Scheme VI).

DETAILED DESCRIPTION

According to aspects of the present inventions, the use of implantable devices within the body often creates the need for devices which are biocompatible, biodegradable and/or radiopaque. Among these areas of therapeutic practice employing implantable devices are interventions for diseases or conditions affecting body lumens, such as arteries, veins, various organ ducts, gastrointestinal, urinary, and the like. In addition, treatments in, or surrounding, joints require devices that are able to withstand the complex forces associated with these unique body areas.

Certain embodiments comprise bioresorbable polymer scaffolds, suited for use in diseased vessels of the circulatory system, particularly in vessels affected by peripheral artery disease. A particular aspect of certain embodiments having aspects of the invention includes the employment of cross-linked (X-linked) polymer materials, providing a tough resilient framework.

The formation of a sufficient number or density of these cross-links within the material enhances the properties so as to create a tough elastic, generally crush-recoverable, material.

Examples of polymer embodiments having aspects of the invention may comprise copolymers which have a rubbery or partially rubber state as initially synthesized and isolated, for example, a copolymer having a Tg (glass transition temperature) less than 37° C. In certain examples, this desired property may be achieved by incorporation in the copolymer of macromers such as PCL (polycaprolactone), PTMO (polytetramethylene oxide), PTMC (polytrimethylene carbonate), PEG (polyethylene glycol), and the like, polydioxanone and co-macromers thereof.

In embodiments of methods having aspects of the invention, a partially rubber polymer material may be prepared which has moieties or functional groups incorporated along polymer chains which have a latent capability of crosslinking by reaction with sites on adjacent polymer chains (initial material state or unlinked material state). Such a material may be described as a latently cross-linkable polymer material.

The polymer material in the initial unlinked material state may be formed into a physical configuration suitable for a desired device or product (pre-form). Note, such a pre-form configuration may closely resemble a desired final product or device; or alternatively may have an intermediate configuration suitable for subsequent processing.

A pre-form as described above may then be subjected to conditions suited to activate the latent cross-linking moieties on the polymer so as to produce a cross-linked polymer device or product comprising a polymer material in a cross-linked material state, so as to provide desired properties (toughness, resilience, and/or crush recoverability, and the like). In an example embodiment, a latently-crosslinkable copolymer material in an initial unlinked state may be pre-formed into a tubular shape (such as by sheet rolling, dip coating, extrusion/blow molding or the like). The tubular preform is subsequently exposed to conditions (e.g., heat, radiation, chemical or solvent application) suited to activate the cross-linkable moieties.

Polymer material embodiments having aspects of the invention may be made according to a number of schemes, examples of which are described below.

Scheme I—Latently Cross-Linkable Pendent Group on Monomer/Macromer

Scheme I includes a general exemplary approach to making a cross-linked bioresorbable polymer device. FIG. 2 is a flowchart showing the steps of Scheme I, which may be outline as follows:

A. First Component Having a Pendant Functional Group

A polymer material is prepared which has a first biodegradable (and optionally radiopaque) monomer or macromer component which has a pendant moiety or functional group which is ultimately suitable for cross-linking reactions, but which is protected or otherwise insulated from internal cross-reactions ("latently cross linkable component"). Examples include I$_2$DTtBu (I$_2$-desaminotyrosyl-tyrosine tert-butyl ester) and its macromers, or component with acryloyl or methacryloyl moiety in the pendant group and the like and mixtures thereof. The protected functional group on the side chain is converted to a crosslinkable group after the polymer is prepared. The crosslinkable group should remain unreacted during preforming steps by various means, e.g., heat treatment, solvent casting or 3-D printing. The crosslinking then occurs only in the subsequent stage of initiation, e.g., by heating, radiation, or other means. The first component may be made of one or more compounds.

B. Second Component having "Rubbery" or Elastic Properties

The polymer material includes also a second generally rubbery biodegradable component (macromer or monomer) which serves to influence the copolymer thermo/mechanical properties, such as the Tg or glass transition temperature ("rubbery component"). Examples include, without limitation, PCL (polycaprolactone), PTMO (polytetramethylene oxide), PTMC (polytrimethylene carbonate)), PEG (polyethylene glycol), polydioxanone and the like and co-macromers thereof.

Note that in this example, the component having a pendant functional group ("A") and the component having "rubbery" properties ("B") are described as distinct ingredient components. In alternative embodiments a component with "rubbery" properties may also have a pendant functional group suitable for cross-linking as described below.

C. Polymerization Reaction to Create a Latently Cross-Linkable Copolymer

The first latently cross-linkable component is co-polymerized with the second rubbery component to form a copolymer material. The pendent moiety is unreactive (e.g., a tert-butyl ester) during the copolymerization process. Thus the copolymer may be isolated without triggering cross-linking. Note that, in certain embodiments, either or both components may contain latently cross-linkable groups.

After the copolymerization process the pendent moiety is converted into an active form such as methacryloyl moiety (for free radical crosslinking) or other moieties that can react via nucleophilic substitution. During the pre-form process, however, these activated moieties still remain inactive. The crosslinking process is carried out on the pre-forms.

D. Pre-Form Version of the Desired Device

The latently X-linkable copolymer may be formed into a desired functional configuration and/or shape using processes that do not initiate X-linking of the pendant functional groups ("pre-form"). Such a pre-form version of the desired device may have a form which is a selected approximation of the final device form. In an exemplary vascular scaffold pre-form, such processes as dip-coating, sheet pressing and rolling, blow-molding, and the like may be employed, and the pre-form thus created may be a tubular shape, suitable in dimensions for subsequent laser-cutting operations. The tube (or other pre-form) may then be adapted as desired for a particular purpose. For example, a tube pre-form may be cut by lasers to a pre-determined pattern of rings and interconnects to form a series of rings of a stent or scaffold, such as for vascular support.

E. Pre-Form Subjected to Cross-Linking Triggering Conditions

The pre-form comprising latently X-linkable copolymer material may subsequently be subjected to conditions which trigger cross-linking reactions between polymer chains. Examples include esterification reactions, and the like, or free radical polymerization of available methacryloyl moieties. Triggering conditions may include heat, radiation, solvent or free radial initiator incorporation followed by heat or radiation, and the like. The crosslinking results in substantial changes to the thermo-mechanical properties of the preform material, for example creating a tough, resilient, impact-resistant and/or crush recoverable structure.

Note that the pre-form version of the desired device for Step E may have a form which is a selected approximation of a final device form. Thus, in certain embodiments, the pre-form may have a form and shape intended to be used in final form after the cross-linking of Step E. In other embodiments, the pre-form may have a size and/or shape suited to subsequent optional processing (not shown in FIG. 2), such as machining, etching, coating, and the like, prior to use.

Although the pre-from may consist solely of the latently crosslinkable copolymer material of Step E, in still further embodiments, the pre-form may comprise other components or materials as well. For example, a preform may include an assembly of interconnected parts in which some parts comprise the latently X-linkable copolymer material of Step E, while other parts comprise a material which is not latently cross-linkable (e.g., metal components).

Scheme II—Crosslinking Via Transesterification

In one exemplary embodiment having aspects of the invention is a scheme for making a cross-linked biodegradable, radiopaque polymer material and related device by means of transesterification.

FIG. 3 illustrates step-wise the chemical reactions and steps of Scheme II:

A. Forming a Copolymer Having Protected Functional Groups

In the particular exemplary embodiment illustrated, the precursor groups include I2DTE (di-iodinated desaminotyrosyl tyrosine ethyl ester), I2DTtBu (tert-butyl substituted I2DTE)—the component with protected functional group which lately could be converted in X-linkable group, and a diol or hydroxy-terminated macromer of the structure HO-M-OH, where M is a low Tg macromer selected from the group including PTMC, PTMO, PCL, PEG, PLLA, PGA, PLGA, polydioxane and the like and copolymers thereof. The precursor components may be linked via phosgenation, as exemplified by the description of Example 2 herein. A functional site on a precursor group may be protected from reaction during polymerization, such as by the tert-butyl group of I2DTEtBu. Note that in the example illustrated, a, b, and c indicate the percent composition of each precursor, each of which can vary from 0 to 100%, so that a+b+c=100%.

B. Elimination of Protecting Pendant Group and Formation of Latently-Linkable Functional Groups The copolymer material may then be esterified with a latently-linkable group. This process may first include elimination of a protecting pendant group, e.g, a tert-butyl protecting group in the example shown. In the particular embodiment illustrated, the linkable group has the structure HZCH$_2$—X—CH$_2$—OH, wherein Z is selected from the group consisting of O, S, and NH; and X is selected from the group consisting of a bond, an alkylene group, or an alkenelene with 1-10 carbon atoms, and a substituted or unsubstituted phenylene group. EXAMPLE 4 below describes an esterification with 1,3-propanediol as a latently-linkable group. EXAMPLE 6 below describes an esterification with ethanolamine as a latently-linkable group (i.e., Z=NH).

C(1). Forming into a Device Pre-Form

A pre-form having a selected size and shape (e.g., of a medical device such as a stent) may be formed to include the copolymer material of Step B.

C(2). Heating to Induce Transesterification

Heat may be applied to induce or trigger transesterification in which the linkable group (e.g. 1,3-propanediol) bonds to an adjacent vulnerable site on a polymer chain of the copolymer material, for example as described in EXAMPLE 5.

Scheme III—Crosslinking Via Free Radical Addition

In another exemplary embodiment having aspects of the invention is a scheme for making a cross-linked biodegradable, radiopaque polymer material and related device, the cross-linking may be achieved by means of via free radical addition.

FIG. 4 illustrates step-wise the chemical reactions and steps of Scheme III:

A. Forming of Copolymer Having Protected Functional Groups

In the particular exemplary embodiment illustrated, the precursor groups include I2DTE (di-iodinated desaminotyrosyl tyrosine ethyl ester), I2DTtBu (tert-butyl substituted I2DTE)—the component with protected functional group which later could be converted in X-linkable group, and a diol or hydroxy-terminated macromer of the structure HO-M-OH, where M is a low Tg macromer selected from the group including PTMC, PTMO, PCL, PEG, PLLA, PLGA, polydioxane and co-macromers thereof; and wherein a, b, and c indicate the percent composition of each precursor, each of which can vary from 0 to 100%, so that a+b+c=100%.

As in Scheme II above, the precursor components may be linked via phosgenation, and a functional site on a precursor side chain may be protected from reaction during polymerization, such as by the tert-butyl group of I2DTtBu.

B. Elimination of Pendant Groups and Formation of Latently-Linkable Functional Groups As in Scheme II, the copolymer material may then be esterified with a latently-linkable group. In the embodiments shown in FIG. 4, this group is a HEMA-like group: e.g., where Z=O the group comprises 2-hydroxyethylmethacrylate (HEMA). In other embodiments, the HEMA-like group may be 2-aminoethyl methacrylate hydrochloride (AEMA). See EXAMPLES 9, 12, 13 and 14 in this regard. This process may first include elimination of a protecting pendant group, e.g., a tert-butyl protecting group in the example shown. The HEMA-like group can be coupled to the COOH group using, for example, the procedure described in EXAMPLE 9 below for AEMA as the HEMA-like group.

C(1). Forming into a Device Pre-Form

A pre-form having a selected size and shape may be made as described in SCHEME II above.

C(2). Heating with a Free Radical Initiator to Induce Cross-Linking

A free radical initiator such as AIBN may be applied, together with heat, to induce cross-linking, such as be the method described in EXAMPLE 19 below.

Note that, as described in EXAMPLES 21 and 22 below, one or more free radical initiators (e.g., AIBN) may be introduced during the device fabrication process, and may be distributed within the latently cross-linkable polymer material. Examples include spray casting/coating and dip-casting, wherein the initiator may be dissolved or suspended in the solvent along with the latently cross-linkable copolymer.

Alternative Monomers in Schemes II and III

In both scheme II and III, the DTtBu can be replaced with t-butyl ester of diphenolic acid whose structure is given below.

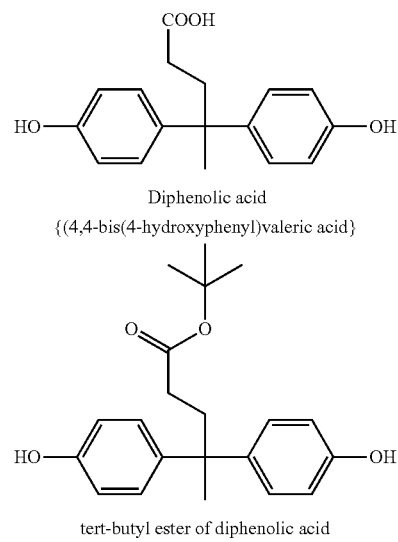

Diphenolic acid
{(4,4-bis(4-hydroxyphenyl)valeric acid} tert-butyl ester of diphenolic acid

Additionally, glycerol, trifunctional polycaprolactone, trifunctional PTMC, etc. with suitable modification can be used for crosslinking purposes.

Scheme IV—Using PrD-di I2DAT Instead I2DTE

FIG. 5 illustrates step-wise the chemical reactions and steps of SCHEME IV. In this particular example, the methods are similar to those of SCHEME III. In this embodiment, one precursor comprises propane-1,3-diyl bis(3-(4-hydroxy-3,5-diiodophenyl)propanoate), also known as PrD-di I2DAT, in place of (or in combination with) I$_2$DTE. The meaning of terms are otherwise that as described as for SCHEME III.

Scheme V—Polymer with Crosslinkable Group in Rubbery Components

FIG. 6 illustrates steps of SCHEME V, including preparing latently crosslinkable polymers. In this particular example, a crosslinked polymer device is made from latently-crosslinkable polymers comprising TMC oligomeric diols with pendant groups containing double bonds (HEMA-like groups), in which the TMC oligomeric diols may copolymerized with a range of different oligomer or macromer diols, the particular diols selected to give desired properties to the resulting polymeric structural material. Embodiments having aspects of the inventions herein are suited to use in implantable devices requiring resilience and crush-recover capability. Examples of such devices include stents for peripheral artery treatments, such as SFA (superficial femoral artery) stents and the like.

A. Preparation of Oligomeric TMC Diol Having Pendant HEMA-Like Group

In an initial step, an oligomer is prepared from glyceryl monomethacrylate (commercially available, e.g., from PolySciences Inc) and TMC (trimethylene carbonate), using suitable catalysts (see EXAMPLE 15, below). The resulting oligomer is hydroxy-terminated, a diol, and comprises chains of polymerized TMC including at least one pendent HEMA-like group coming from glyceryl monomethacrylate components. The TMC oligomeric diol may be referred to as a "chain extension group", and the pendant HEMA-like may be referred to as a "cross-linking group". For convenience, this resulting oligomer (or mixture of similar oligomers) may be referred to as "OligoTMC/HEMA".

B. Co-Polymerization with Selected Monomer, Macromer or Oligomer Diols

The "OligoTMC/HEMA" from Step A may be reacted with other diols so as to produce a copolymer of selected composition. For example, diols may be selected from PTMC, PTMO, PCL, PEG, PLLA, PG, polydioxane and co-macromers thereof, and the like. In embodiments, the diols may include monomers, macromers or oligomer comprising compounds described below: I2DTE, PrD-di I2DAT, and the like.

The polymerization may be accomplished using such reactants as triphosgene (TP), oxalyl chloride, and the like, and mixtures thereof, which produce bonds between adjacent diols (e.g., carbonate bonds and/or oxalyl ester bonds).

In certain embodiments, a copolymer material may have a portion of oxalyl ester bonds in the polymer chain in a sequence with carbonate bonds. Such a mixture of bond types may be used to "tune" the biodegradation properties of the polymer material. Note that the copolymerization process may be carried out in various modes of reaction sequence, such as simultaneous reaction mixtures, sequential reactions, alternating reactants (e.g., alternating addition of TP and oxalyl chloride to a reaction mixture), and the like.

C. Forming into a Device Pre-Form, Introducing a Free-Radical Initiator, and Cross-Linking to Form the Device Theses steps may be carried out as described above with respect to Schemes III and IV.

Scheme VI—Polymer with Multiple Cross-Linkable Groups

In schemes II, III and IV the crosslinkable functional groups were present on structural, non rubbery component of copolymer, while in the scheme V the cross-linkable functional groups were present on rubbery component. Copolymerization of components containing tert-butyl group (I2DTtBu) and components similar to "OligoTMC/HEMA" will lead to incorporation of two different types of latently cross-linkable functional groups.

FIG. 7 illustrates steps of SCHEME VI, in which an example copolymer "structural" portion similar to that of FIG. 5 (having a protective group) is polymerized with an example copolymer "rubbery" portion similar to that of FIG. 6 (comprising oligomeric TMC with a HEMA-like pendant group). Using methods describe herein, the protective group is eliminated from the structural portion, and a HEMA-like functional group attached.

The resulting multi-functional copolymer material may then be formed into a device pre-form, and subsequently cross-liked by activation of a free radical initiator as described herein. Note that such cross-links may form between either "rubbery-to-rubbery" components, "structural-to-structural" components, or rubbery-to-structural" components.

Non-Iodinated Embodiments

Note, that while various figures and Schemes illustrated herein may include certain halogenated (iodinated) versions of the chemical structures and moieties described, the various embodiments of the polymer materials having aspects of the invention may also include non-halogenated (non-iodinated) embodiments of these structures and schemes. For example, non-iodinated latently cross-linkable or cross-linked polymer materials may be suited to uses in medical devices where radiographic visualization is not needed.

Additional Alternatives

Note that other monomers may be substituted for I2DTE and PrD-di DAT shown above. Methods for making and using these are described in U.S. Pat. Nos. 6,284,862; 6,475,477; 8,685,367; 7,473,417; 8,008,528; 8,461,289; 8,551,511; 8,252,887; 8,415,449; 9,080,015; 8,765,161; 9,605,112; 8,883,861; 9,416,090; 2015-0045,451; and 2016-0177,028, among other publications (each of which is incorporated herein by reference).

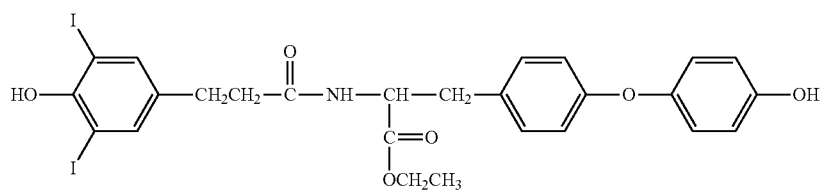

I2DAT-Thyronine ethyl ester
Example 7 of U.S. Pat. No. 8,461,289 (Fox-726)

For example, the above referenced U.S. Pat. No. 6,475,477 describes as Formula I the following:

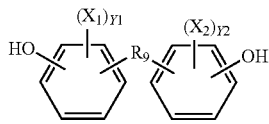
(I)

wherein Formula I represents a diphenol compound substituted with at least one bromine or iodine atom, wherein each $X_1$ and $X_2$ are independently an iodine or bromine atom, Y1 and Y2 are independently between zero and two, inclusive, and R9 is an alkyl, aryl or alkylaryl group with up to 18 carbon atoms.

Further description of both Formula I and various other monomers and polymers from U.S. Pat. No. 6,475,477 are incorporated by reference herein. Such monomers and polymers may be included in embodiments polymeric materials herein by one of ordinary skill in the art without departing from the spirit of the inventions described herein.

Drug/Pharmaceutical Agent Coating

A device made from embodiments of polymer materials described herein may be an implantable device having a content of a drug or pharmaceutical agent. For example, the device may comprise a stent or scaffold suited for vascular implant, and may include a drug/agent in a coating. Drug-eluting stents (DES) have included drug coating on all or a portion of the structure, the coating comprising a drug agent, such as an anti-restenosis drug (e.g., Sirolimus, paclitaxel, everolimus, and the like) in a carrier polymer. Various other therapeutic agents or drugs have been suggested, see for example, European Patent EP1789097. A coating of a drug-eluting stent may comprise a coating polymer which is biodegradable, so as to release the drug as the coating degrades.

EXAMPLES

Additional embodiments are disclosed in further detail in the following schemes and examples, which are not in any way intended to limit the scope of the claims.

Example 1

Preparation of Poly(trimethylene carbonate) PTMC 8.5K

The following example illustrates preparation of PTMC macromer of 8.5 KDa. Into a 500 mL 2-necked flask equipped with an overhead stirrer and a nitrogen inlet tube were added trimethylene carbonate (250 g, 2.45 mol), ethylene glycol (1.5 g, 0.025 mol).

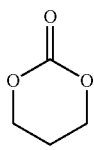

Trimethylene carbonate

The flask was placed in an oil bath at 110° C. while being stirred with a stainless steel stirrer under dry nitrogen atmosphere. After the solids completely melted the temperature of the oil bath was increased to 130° C. To the reaction mixture was then added 0.15 g of Sn(II) octoate with a pre-weighed 1 mL syringe. Stirring was continued for 3.5 h and then allowed to cool to room temperature. The viscous oil was transferred to a 1 L beaker using 200 mL of dichloromethane. The polymer was precipitated as thick oil by adding 250 mL of heptane with stirring. The product was further purified by dissolving in 200 mL of dichloromethane and precipitating with 250 mL of heptane. The thick syrupy polymer was dried under vacuum at ambient temperature. The $^1$H NMR showed a Mn of 8.5K.

EXAMPLES 2, 3, 4, and 5 below herein collectively illustrate examples suitable for preparation of a Terpolymer with pendent propanediol functional groups (latently cross-linkable), which may then be crosslinked with heat.

Example 2

Preparation of Poly(50% I2DTE-co-10% I2DTtBu-co-40% PTMC8.5K carbonate)

Into a 1 L, 3-necked flask were added 25 g of I2DTE, 5 g of I2DTtBu, 20 g of PTMC 8.5K prepared according to EXAMPLE 1, and 265 mL of dichloromethane (DCM). The mixture was stirred with an overhead stirrer at 300 rpm and 16.25 mL of pyridine was added when all the solids went into solution. Triphosgene (5.32 g) was dissolved in 15 ml of dichloromethane and was transferred to a 25 ml syringe. Using a syringe pump the content of the syringe was added to the flask at a rate of 6.3 mL/min until the reaction mixture became viscous. The reaction was quenched by adding a mixture of 45 mL of THF and 5 mL of water. While stirring at 300 rpm, 450 mL of 2-propanol (IPA) was added to the flask to precipitate the polymer. Stirring was continued for 30 minutes and then allowed to settle. The supernatant was siphoned off and the residue was stirred with 225 mL of IPA for 30 min and after the polymer settled to the bottom of the flask the supernatant was siphoned out. This was repeated with 100 mL of IPA. The product was isolated by filtration. The polymer was re-purified by dissolving in 250 mL of DCM and precipitating with 375 mL of IPA. The precipitate was dried in vacuum oven at 45° C. for 24 h. The 1H NMR of the polymer was consistent with the composition.

Example 3

Elimination of Tert-Bu Protecting Group to Form Poly(50% I2DTE-co-10% I2DT-co-40% PTMC8.5K Carbonate)

Tert-Bu protected group is converted to COOH group by using trifluoracetic acid (TFA). Trifluoracetic acid (100 mL) was placed in a 1 L flask and stirred with an overhead stirrer. The polymer from EXAMPLE 2 was added to the flask and as the polymer dissolved the solution became very viscous. To the flask was then added 100 mL of DCM and stirred overnight with fumes from the flask directed into a bottle containing NaOH solution. The polymer was precipitated with 400 mL of IPA while stirring at 300 rpm. The polymer precipitated as fine particles. After removing the supernatant by siphoning the polymer was stirred twice with 100 mL portion of IPA and filtered each time. The polymer was washed with two 100 mL portions of heptane. It was dried in the vacuum oven at 45° C. for 4 h and then at 55° C. for 2 days.

Example 4

Esterification of Poly(50% I2DTE-co-10% I2DT-co-40% PTMC8.5K Carbonate) with 1,3-propanediol The reaction was carried out with a large excess of 1,3-propane diol in order to ensure that all the acid groups in the polymer are esterified and also to prevent crosslinking at this stage.

Into a 500 mL round-bottomed flask with an overhead stirrer and modified Dean-stark trap for solvents heavier than water, was placed 8 grams of the polymer from EXAMPLE 3, 2.3 grams of 1,3-propanediol, 0.5 g of p-Toluenesulfonic acid monohydrate (PTSA), and 200 mL of 1,2-dichloroethane.

The flask was heated using an oil bath maintained at 108° C. Reflux was carried out 8 h. Molecular sieves were placed in the side arm of the Dean-stark trap to remove trace amount of water generated from the reaction. The reaction mixture was cooled to room temperature and the contents were added to a 1 L beaker. The polymer was precipitated by adding 750 mL of IPA while stirring with an overhead stirrer. The precipitate was washed with IPA and then dissolved in 80 mL of DCM and precipitated with heptane. The precipitate was washed with heptane and dried in vacuum oven at 45° C. for 24 h. DSC of the sample gave Tg of −12.5° C.

The $^1$H NMR showed three new peaks (corresponding to the 3 methylene groups of 1,3-propanediol —O—CH$_2$—CH$_2$—CH$_2$—OH at 4.2, 1.7, and 3.41 ppm respectively.

Example 5

Preparation of Polymer Films and Crosslinking of the Polymer (a) Films were prepared by compression molding 0.5 g of Poly(50% I2DTE-co-10% I2DT-O—CH$_2$CH$_2$CH$_2$OH-co-40% PTMC8.5K carbonate) prepared in EXAMPLE 4 at 140° C. A strip of the film was rolled into a tube and the ends were glued together using DCM. The tube was dried in vacuum oven at 45° C. for 5 h.

(b) The tube was then placed inside a small culture tube which was immersed in an oil bath at 160° C. A Pasteur pipette was inserted through the polymer tube and nitrogen gas was passed through the Pasteur pipette at a slow rate. The polymer tube shrank and became stiff. Some bubbles were also observed throughout the tube due to evolving ethanol vapors.

(c) The culture tube was taken out of the oil bath after 15 min and allowed to cool to room temperature. A piece of the polymer tube was placed in another culture tube and some DCM was added to it and vortexed. The piece of the tube did not dissolve, instead it swelled indicating crosslinking.

Example 6

Preparation of Poly(50% I2DTE-co-10% I2DT-O—NHCH2CH2OH-co-40% PTMC carbonate) with Pendent Ethanolamine Functional Groups (Latently Cross-Linkable), which May then be Crosslinked with Heat Into a 500 mL 2-necked flask equipped with an overhead stirrer and a nitrogen inlet were added 20 g of polymer obtained in EXAMPLE 3 (deprotected polymer), 200 mL of tetrahydrofuran (THF), 0.13 g of ethanolamine, 0.11 g of hydroxybenzatriazole, and cooled in ice-water bath. The addition of ethanolamine gave a light reddish brown color. To the flask was then added EDCI (0.27 g) when reaction mixture became colorless.

After stirring for 2 h the ice-water bath water was removed and the reaction mixture was allowed to warm to room temperature (20° C.) and 0.2 g of additional EDCI was added and stirred for 1 h.

To quench the reaction and precipitate the polymer 200 mL of DI water was added. The precipitate was isolated by filtration and washed with water. The polymer was dried in a vacuum oven at 45° C. for 24 h. The product was then dissolved in 200 mL of THF and while stirring at 400 rpm, 200 mL of IPA was added and then allowed to stand undisturbed for 30 min. The supernatant was siphoned out and the fine soft precipitate was stirred with 100 mL of IPA, allowed to stand and the supernatant was siphoned out. The last step was repeated with 50 mL of IPA.

The precipitate was isolated by filtration, washed with IPA and finally dried in vacuum oven at 45° C. for 4 days. $^1$H NMR (dmso-d6) showed a new peak at 8.12 ppm corresponding the amide NH. The other two peaks due to CH$_2$ groups were obscured by the H$_2$O peak at 3.4 ppm.

The film preparation and crosslinking was carried out as in EXAMPLE 5.

EXAMPLES 7, 8 and 9 collectively illustrate examples suitable for preparation of a Terpolymer Poly(45% I2DTE-co-10% I2DT/AEMA-co-45% PTMC10K carbonate), similar to Terpolymer from EXAMPLE 5 with Propane diol based X-linking group and Terpolymer from EXAMPLE 6 with Ethanol amine based X-linking group, but has 2-aminoethyl methacrylate (AEMA) based pendant function groups.

Example 7

Preparation of Poly(45% I2DTE-co-10% I2DTtBu-co-45% PTMC10K carbonate)

Into a 1 L 3-necked flask equipped with an overhead stirrer, a nitrogen outlet, and syringe pump inlet were added 22.5 g of I2DTE, 22.5 g of PTMC10K, and 5 g of monomer of I2DTtBu. The monomers were dissolved by stirring with 270 mL of chloroform and 12 mL of pyridine. To the stirred solution was added 4.2 g triphosgene dissolved in 18 mL of chloroform using syringe pump until the reaction mixture became very viscous. It was quenched with a mixture of 5 mL of water in 45 mL of THF.

Polymer was precipitated by adding 450 mL of IPA to reaction mixture while stirring at 300 rpm. Stirred for additional 60 min and the supernatant was siphoned out. The precipitate was washed with 250 mL of IPA. The polymer was dissolved in 300 mL of DCM and precipitated with 500 mL of IPA. The precipitate was isolated by filtration and dried in vacuum oven at 30° C. for 1 h and then additionally dried at 65° C. for 24 h.

Example 8

Elimination of tert-Bu Protecting Group to Form Poly(45% I2DTE-co-10% I2DT-co-45% PTMC 10K Carbonate)

The 40 grams of polymer from EXAMPLE 7 was stirred with 200 mL of DCM for 3 h to dissolve in a 1 L round bottomed flask. When the polymer was completely in solution, 200 mL of trifluoroacetic acid was added and stirred at room temperature overnight. To the reaction mixture with vigorous stirring was added 100 mL of IPA and the resulting solution was transferred to a 1 L beaker and precipitated by adding 200 mL of IPA with vigorous stirring. The supernatant was siphoned out and the precipitate was further stirred with 100 mL of IPA. The washing was repeated with another 100 mL portion of IPA. The precipitate was dried in a vacuum oven at 40° C.

Example 9

Coupling Aminoethyl Methacrylate (AEMA) to Poly(45% I2DTE-co-10% I2DT-co-45% PTMC10K carbonate)

10 grams of terpolymer from EXAMPLE 8 was dissolved in 125 mL of Tetrahydrofuran in a 250 mL round bottomed flask and stirred with an overhead stirrer under nitrogen atmosphere. AEMA.HCl (0.185 g) and triethyleamine (0.168 g) were added to the stirred reaction mixture.

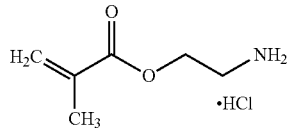

2-Aminoethyl Methacrylate Hydrochloride (AEMA)

To the flask was then added 0.145 g of EDCI and continued to stir for 3 h. The polymer was precipitated by adding 100 mL of IPA to the reaction mixture. The polymer was re-dissolved in 100 mL of THF and precipitated with 100 mL of IPA. The last step was repeated one more time. The precipitate was successively washed with 50 mL of IPA and 25 mL of IPA. It was then dried in the vacuum oven at 40° C. overnight. The $^1$H NMR spectrum of the product showed two singlets at 5.655 and 6.040 ppm corresponding to the two vinyl protons.

See further EXAMPLE 14 for Crosslinking films made from polymer in EXAMPLE 9.

EXAMPLES 10, 11 AND 12 collectively illustrate examples suitable for preparation of Poly(50% I2DTE-co-10% I2DT/AEMA-co-40% PTMC10K carbonate with 2-aminoethyl methacrylate (AEMA) based pendant function groups.

Example 10

Preparation of Poly(50% I2DTE-co-10% I2DTtBu-co-40% PTMC10K carbonate)

Into a 1 L 3-necked flask equipped with an overhead stirrer, a nitrogen outlet, and syringe pump inlet were added 25 g of monomer I2DTE, 20 g of PTMC10K, and 5 g of monomer I2DTtBu. The monomers were dissolved by stirring with 270 mL of chloroform and 16 mL of pyridine. To the stirred solution was added 5.9 g triphosgene dissolved in 16 mL of chloroform until the reaction mixture became very viscous. It was quenched with a mixture of 5 mL of water in 45 mL of THF. Polymer was precipitated by adding 450 mL of IPA to reaction mixture while stirring at 300 rpm. Stirred for additional 60 min and the supernatant was siphoned out. The precipitate was washed with 250 mL of IPA. The polymer was dissolved in 300 mL of DCM and precipitated with 500 mL of IPA. The precipitated polymer was isolated by filtration. The polymer was dried in vacuum oven at 30° C. for 1 h and then dried additionally at 65° C. for 24 h.

Example 11

Elimination of tert-Bu Protecting Group to Form Poly(50% I2DTE-co-10% I2DT-co-40% PTMC10K Carbonate)

45 grams of the polymer from EXAMPLE 10 was stirred with 500 mL of DCM for 2 h to dissolve in a 1 L round bottomed flask. When completely in solution, 370 mL of trifluoroacetic acid was added and stirred at room temperature overnight. To the reaction mixture with vigorous stirring was added 200 mL of IPA and the resulting solution was transferred to a 1 L beaker and precipitated by adding 250 mL of IPA with vigorous stirring. The supernatant was siphoned out and the precipitate was dissolved in 500 mL of DCM. The polymer was precipitated out with 250 mL of IPA. After removal of the supernatant the precipitate was stirred with 250 mL of IPA. The product was isolated by filtration and washed with twice with 100 mL of IPA. The product was transferred to a stainless steel pan and dried in vacuum oven at 40° C. for 2 days.

Example 12

Coupling Aminoethyl Methacrylate (AEMA) to Poly(50% I2DTE-co-10% I2DT-co-40% PTMC10K carbonate)

20 g of polymer from EXAMPLE 11 were converted to polymer with aminoethyl methacrylate pendent chain using procedures similar to that described in EXAMPLE 9. The obtained polymer was dried at 50° C. for 5 days in vacuum oven.

EXAMPLE 13 illustrates an example suitable for preparation of a Terpolymer similar to Terpolymer from example 12, which contains both COOH and AEMA pendant chains. Keeping COOH pendant chain in resulting copolymer might accelerate rate of biodegradation.

Example 13

Preparation of Terpolymer Containing Both COOH and 2-amidoethylmethacrylate (AEMA) Functional Groups Using procedures similar to EXAMPLE 10 a terpolymer Poly(40% I2DTE-co-20% I2DTtBu-co-40% PTMC10K carbonate) was prepared. The tert-butyl group of the terpolymer was converted to COOH group by using trifluoroacetic acid. Only ½ the amount COOH groups were converted to the 2-amidoethylmethacrylate group by reacting with calculated amount of 2-aminoethylmethacrylate and EDCI.

Example 14

Crosslinking Films Made from Polymers of Examples 9, 12 and 13

A 0.2 mm thick film of polymer prepared as in EXAMPLE 9 was prepared by compression molding at 175° C.

A piece of the film when stirred with DCM dissolved within minutes indicating that no crosslinking occurred during compression molding.

A solution containing 100 mg of AIBN in 2 mL of acetone was prepared and diluted with 2 mL of heptane.

A strip of the film was immersed in the AIBN solution for 2 min.

The film was dried in vacuum oven at 40° C. for 5 min. The film was heated in an oil bath at 100° C. for 10 min. The film was blotted dry and immersed in DCM. The film did not dissolve even after a few days in DCM.

Films from EXAMPLES 12 and 13 were compression molded and cross-linked by similar way.

Alternate Examples 9, 12, and 14 with HEMA: 2-hydroxyethylmethacrylate (HEMA) instead of AEMA can be coupled to the COOH group using similar procedures. In this case a catalytic amount of 4-dimethylamino pyridine (DMAP) is added to accelerate the reaction. See Examples above and FIGS. 4 and 5.

Example 15

Preparation of Oligomeric Trimethylene Carbonate Diols with HEMA-Like Pendant Chains (Precursor-Diol with Double Bonds in the Side Branches for Free Radical Polymerization)

In a 500 mL round-bottomed flask are placed Glyceryl monomethacrylate (20 g, 0.124 mols), trimethylene carbonate (157 g, 1.24 mol) and heated under nitrogen atmosphere till all the solids melt. The flask is then heated at 130° C. and Sn(II)octoate (0.24 g, 500 ppm) is added to the flask. The flask is heated at this temperature for 4 h. The flask is then allowed to cool to room temperature. To remove unreacted monomers and catalyst the product is dissolved in dichloromethane (DCM) and precipitated with heptane twice. The product is dried in a vacuum oven at 30° C. for 24 h. Purity of the product was determined by $^1$H NMR. The product is used without further treatment. In the place of TMC, other compounds such as Lactide (L or D/L), caprolactone, glycolide etc. can be used. For TMC the reaction temperature is lower than the others.

Example 16

Preparation of the Copolymers Containing Precursor-Diol from Example 15

In the second step, oligomeric Precursor (diol) from Example 15, is coupled using triphosgene with one or preferably several monomeric and/or oligomeric diols chosen to give the desirable properties, for example sufficient strength and degradability, to final copolymer. The copolymer components could be PrD-di DAT or/and I2DTE (for strength and radiopacity), oligo PLLA-diol (for degradation and crystallinity), oligo PLDL-diols (for degradation), oligo PGA-diol (for degradation), oligo PCL-diol (for additional elasticity), oligo PTMC-diol (for additional elasticity), or the like.

Example 17

Preparation of Copolymers Containing Oligomeric Precursor TMC/HEMA from Example 15 with Pr-di I2DAT and PLLA7k Diol The copolymer with composition Poly(50% Pr-di I2DAT-co-30% PLLA7k-co-TMC/HEMA1k carbonate) was prepared. Into 1 L 3-necked flask equipped with an overhead stirrer, a nitrogen outlet, and syringe pump were added 75 g of Pr-di I2DAT, 45 g of PLLA7k Diol, and 30 g of "Oligo TMC/HEMA" from REACTION 15. The components were dissolved by stirring with 1000 ml of chloroform and 40 ml of pyridine. To the stirring solution was added 17.8 g triphosgene dissolved in 71.2 ml of chloroform until the reaction mixture became viscous. It was quenched with a mixture of 5 ml of water in 100 ml of THF. The polymer was precipitated by adding 3000 ml of IPA to reaction mixture while stirring at 200 rpm. The supernatant was siphoned out and the precipitate was washed three times with 1000 ml of IPA. The copolymer was re-dissolved in 500 ml of DCM, precipitated with 1500 ml of IPA, and washed three times with 500 ml of IPA. The precipitated copolymer was isolated by filtration and dried in vacuum oven at 55° C. for 24 hours.

Example 18

Preparation of Film Comprising Copolymer of Example 17

A film of polymer from EXAMPLE 17 was prepared by compression molding at 175° C. The film is then turned into a cylindrical shape by wrapping around a metal cylinder the two ends of the film should slightly overlap. To one side of the film a DCM is applied using Q-tip or other device and the other end is pressed over the wet portion of the film. After about 15-20 min the prepared tube is taken off and dried in a vacuum oven at 35-40° C. for 2 h.

Example 19

Introduction of a Free Radical Initiator to the Polymer Tube of Example 18

To introduce free radical initiator into the cylinder, a suitable solvent or mixture of solvents should be chosen. The solvent should dissolve the free radial initiator but it should not dissolve the polymer. The polymer should only swell slightly in solvent so that some initiator gets absorbed into the device. Initiator such as AIBN is dissolved in a solvent (1 to 1 mixture of acetone and heptane, for example). The polymer cylinder is placed in the AIBN solution for known length of time and then taken out and dried in air for 20 min, and then dried in vacuum oven at 50° C. for a few hours.

Example 20

Crosslinking the Polymer Cylinder of Example 19

In this example the cylinder is cross-linked by heating to higher temperature e,g, 100° C. or higher. To test whether the device is cross-linked or not, a piece of the device is added to DCM. If cross-linked, it should not dissolve. The film or cylinder before cross-linking is dissolvable in DCM.

Example 21

Preparation of Tubular Substrates by Spray Coating

Using tubular casting technology such as spray coating to form tubular substrates by spraying solution consisting of mixture of polymers containing HEMA or AEMA functional groups in side branches and free radical initiator AIBN. The tubular substrates prepared by spraying technology are intended for latent cross-linking by free radical polymerization.

Example 22

Preparation of Tubular Substrates by Dip-Coating

Using tubular casting technology such as dip-coating to form tubular substrates from solution of polymers containing HEMA or AEMA functional groups in side branches and free radical initiator AIBN. The tubular substrates prepared by dip-coating are intended for latent cross-linking by free radical polymerization.

Example 23

Preparation of Cross-Linked Films Comprising Copolymer of Example 17 by Solvent Casting Technology A cross-linked film with cross-linking in rubbery phase was prepared from copolymer of EXAMPLE 17 using solvent-casting technology and subsequent thermal treatment. 0.5 grams of copolymer from EXAMPLE 17 and 20 milligrams of free radical initiator AIBN were dissolved in 40 ml of DCM. For complete dissolution 2-3 hours of stirring was used. The solution was cast over flat surface (glass Petri-dish) and left for slow solvent evaporation (at least 10-15 hours at room conditions, followed by vacuum drying). Prepared solvent cast films were cross-linked at temperatures 80-120° C. Optimal duration and temperature of thermal treatment were determined by monitoring residual heat of cure for thermally treated films. The cure was considered complete when no exothermic peak associated with cure was observed on DSC thermograms of thermally treated films.

As in previous Examples, solvent cast films containing AIBN could be rolled into the form of tubular substrates prior to thermal treatment in order to obtain cross-linked tubes suitable, for example, for stent production.

Structures of Compounds Used:

| Name of Compounds | Chemical Structure |
| --- | --- |
| I2DTE {L-Tyrosine,N-[3-(4-hydroxy-3,5-diiodophenyl)-1-oxopropyl]-ethyl ester (3)} | 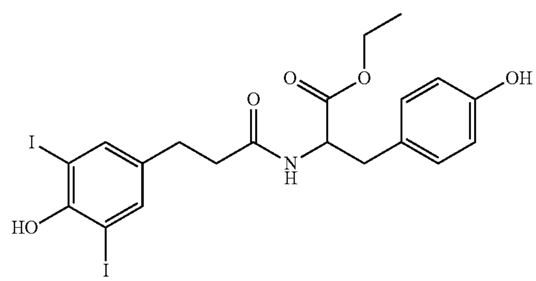 [SMILES: CCOC(=O)C(Cc1ccc(O)cc1)NC(=O)CCc1cc(I)c(O)c(I)c1] |
| I2DTtBu, {L-Tyrosine,N-[3-(4-hydroxy-3,5-diiodophenyl)-1-oxopropyl]-tert-butyl ester (4)} | 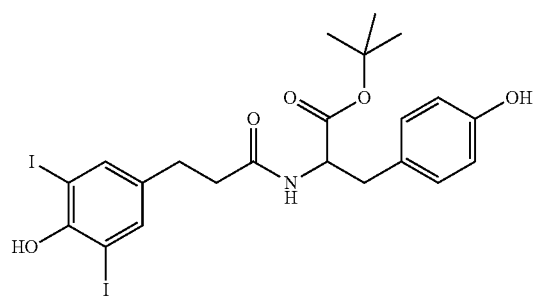 [SMILES: CC(C)(C)OC(=O)C(Cc1ccc(O)cc1)NC(=O)CCc1cc(I)c(O)c(I)c1] |
| PrD-di I2DAT, {propane-1,3-diyl bis(3-(4-hydroxy-3,5-diiodophenyl)propanoate) (5)} | 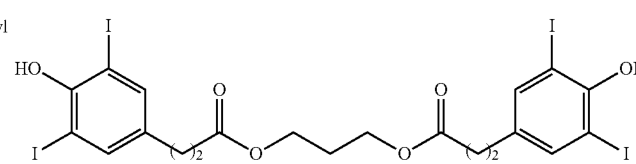 |
| 2-aminoethyl methacrylate hydrochloride (AEMA) | 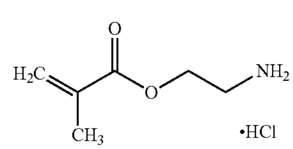 |
| Trimethylene carbonate | |
| 2-hydroxyethyl methacrylate (HEMA) | 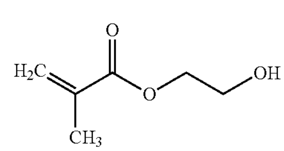 |

All references, patents, applications and articles noted above are in the public realm (whether published online or otherwise), and are incorporated by reference as if fully set forth herein.

References, the contents of which are incorporated in their entireties herein by reference include: J. R. Laird, E. J. Armstrong, *Endovascular Today,* 2014, 13(Suppl):9-11, entitled "An Overview of Superficial Femoral Artery Stenting"; C. D I Mario, H. Griffiths, O. Goktekin, N. Peeters, J. Verbist, M. Bosiers, K. Deloose, B. Heublein, R. Rohde, V. Kasese, C. Ilsley, R. Erbel. *J. Interv. Card,* 2004, 17(6):391-395, entitled "Drug-Eluting Bioabsorbable Magnesium Stent"; M. Peuster, C. Hasse, T. Schloo, C. Fink, P. Beerbaum, C. von Schnakenburg, *Biomaterials,* 2006, 27(28): 4955-4962, entitled "Long-term biocomapatibility of corrodible peripheral iron stent in the porcine descending aorta"; M. Bosiers, Cardiovasc. *Interv. Rad.* 2009, 32(3): 424-435, entitled "AMS INSIGHT-Absorbable Metal Stent Implantation for Treatment of Below-the-Knee Critical Limb Ischemia: 6-Month Analysis"; J. D. Wind, C. Staudt-Bickel, D. R. Paul, W. J. Koros, *Macromolecules,* 2003, 36, 1882-1888, entitled "Solid state covalent cross-linking of polyimide membranes for carbon dioxide plasticization reduction"; M. Werner, A. Micari, A. Cioppa, G. Vadala, A. Schmidt, H. Sievert, P. Rubino, A. Angelini, D. Scheinert, G. Biamino, *JACC Cardiovasc. Interv.* 2014, 7(3):305-312, entitled "Evaluation of Biodegradable Peripheral Igaki-Tamai Stent in the treatment of De Novo Lesions in Superficial Femoral Artery."

The scope of the present disclosure is not intended to be limited by the description of certain embodiments and may be defined by the claims. The language of the claims is to be interpreted broadly based on the language employed in the claims and not limited to the examples described in the present specification or during the prosecution of the application, which examples are to be construed as non-exclusive.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

Certain embodiments of the disclosure are encompassed in the claims presented at the end of this specification, or in other claims presented at a later date. Additional embodiments are encompassed in the following set of numbered embodiments:

Embodiment 1. A biocompatible polymer pre-cure, configured to assume a configuration, comprising elastomeric backbone units (M), non-elastomeric backbone units, and crosslinkable pendant groups, wherein:
at least part of the crosslinkable pendant groups are in a latent form, having a tert-butyl ester end group configured for transesterification, and configured upon activation treatment to convert into an active form, having an acryloyl or ($C_1$-$C_3$ alkyl)acryloyl end group;
at least part of the latent form of the crosslinkable pendant groups are attached to a carbon or nitrogen atom in the elastomeric or non-elastomeric backbone units; and
the crosslinkable pendant groups are configured to react upon cure treatment, thereby curing the biocompatible polymer pre-cure into a biocompatible polymer post-cure.

Embodiment 2. The biocompatible polymer pre-cure of Embodiment 1, wherein:
the latent form of the crosslinkable pendant groups are represented by structural Formula (Ia):

and
the active form of the crosslinkable pendant groups are represented by structural Formula (IIa) or (IIb):

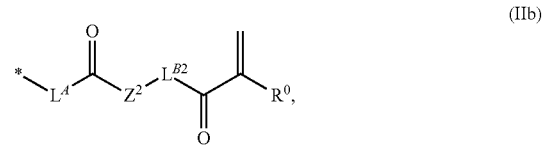

wherein:
* indicates the point of attachment to a carbon or nitrogen atom in the elastomeric or non-elastomeric backbone units;
$L^A$ is a bond or —($C_1$-$C_{10}$)alkylene-;
$Z^1$ and $Z^2$ are each independently O, S, or NH;
$L^{B1}$ is —($C_1$-$C_{10}$)alkylene-, —($C_1$-$C_{10}$)alkenylene-, or —($C_1$-$C_6$)alkylene-phenylene-($C_1$-$C_6$)alkylene-;
$L^{B2}$ is —($C_1$-$C_{10}$)alkylene-O—, —($C_1$-$C_{10}$)alkenylene-O—, or —($C_1$-$C_6$)alkylene-phenylene-($C_1$-$C_6$)alkylene-O—;
the phenylene in $L^{B1}$ or $L^{B2}$ is optionally substituted with 1, 2 or 3 substituents independently selected from ($C_1$-$C_6$)alkyl and halogen; and
$R^0$ is H or ($C_1$-$C_6$)alkyl.

Embodiment 3. The biocompatible polymer pre-cure of Embodiment 1 or 2, wherein the active form of the crosslinkable pendant groups are represented by structural Formula (IIa); and wherein the cure treatment comprises heating and transesterification.

Embodiment 4. The biocompatible polymer pre-cure of Embodiment 1 or 2, wherein the active form of the crosslinkable pendant groups are represented by structural Formula (IIb); and wherein the cure treatment comprises free-radical initiation.

Embodiment 5. The biocompatible polymer pre-cure of any one of Embodiments 1 to 4, wherein the non-elastomeric backbone units comprise recurring groups each independently represented by the structural Formula (IIIa) or (IIIb):

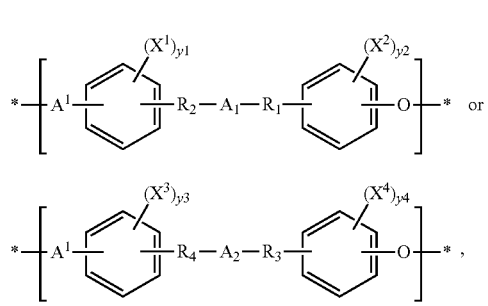

(IIIa)

(IIIb)

wherein:
X¹, X², X³ and X⁴ are each independently Br or I;
y1, y2, y3 and y4 are each independently 0, 1, 2, 3, or 4;
$A_1$, $A_2$ and $A^1$ are each independently selected from the group consisting of

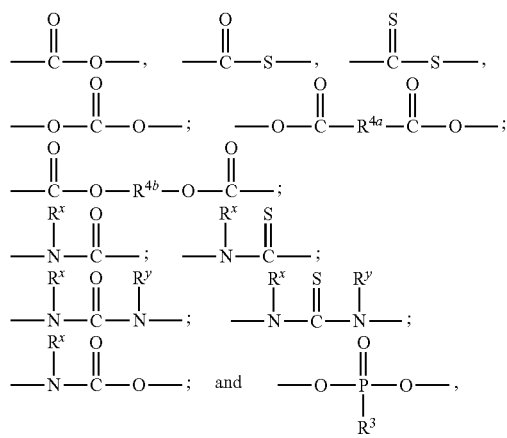

with the proviso that in the event an oxygen-oxygen or oxygen-nitrogen bond is implied by the linking of the $A_1$, $A_2$ or $A^1$ to a neighboring oxygen atom, then that neighboring oxygen atom is absent;
the $A_1$, $A_2$, and $A^1$ groups in Formula (IIIa) or (IIIb) can be integrated from either left-to-right or right-to-left;
$R_1$, $R_2$, $R_3$, $R_4$, $R^{4a}$ and $R^{4b}$ are each independently $(C_1$-$C_{30})$alkylene, $(C_2$-$C_{30})$ alkenylene, $(C_1$-$C_{30})$heteroalkylene, or $(C_2$-$C_{30})$heteroalkenylene, where the heteroalkylene or heteroalkenylene optionally contains 1, 2, or 3 heteroatoms selected from O, S, or N; and
$R^3$, $R^x$ and $R^y$ are each independently H or $(C_1$-$C_6)$alkyl.

Embodiment 6. The biocompatible polymer pre-cure of any one of Embodiments 1 to 5, wherein the non-elastomeric backbone units comprise recurring groups selected from the group consisting of:

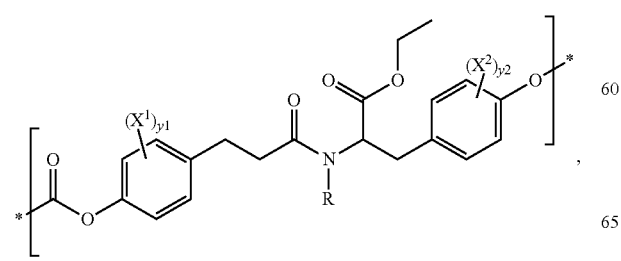

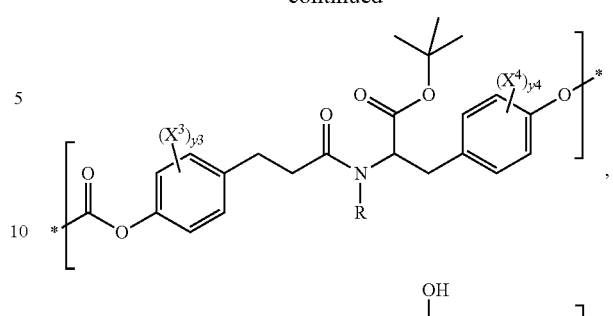

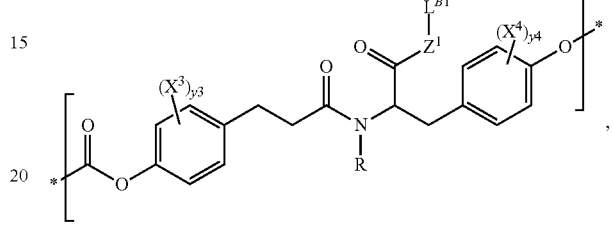

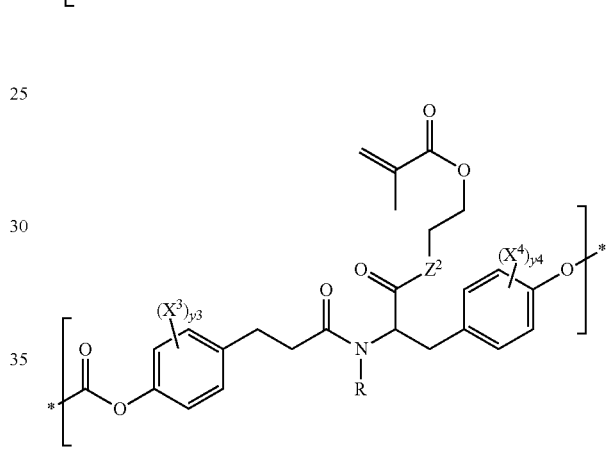

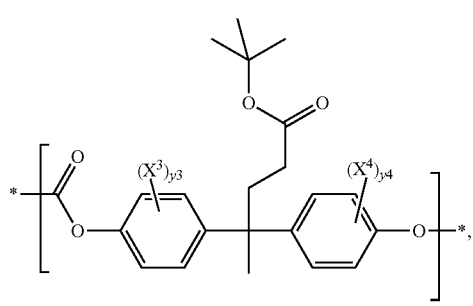

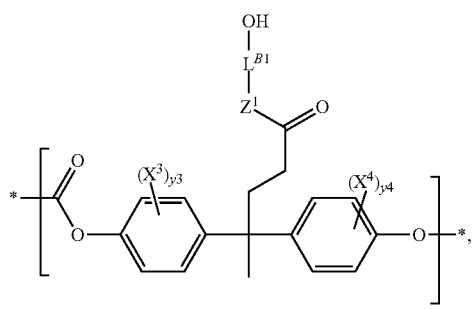

-continued

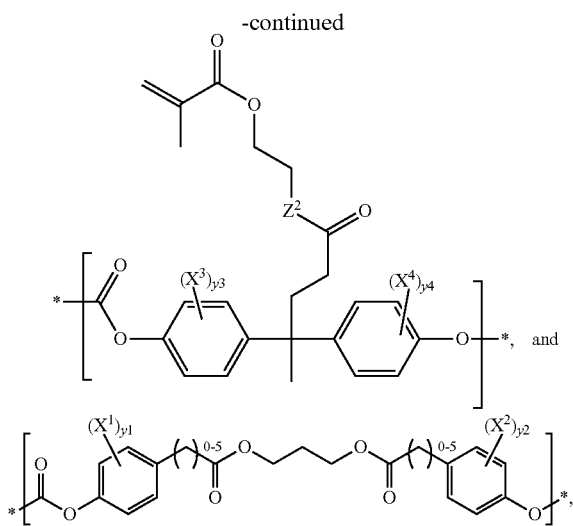

wherein:
R is H or $(C_1-C_6)$alkyl;
Z is O or NH; and
$L^{B1}$ is —$(C_1-C_{10})$alkylene-, —$(C_1-C_{10})$alkenylene-, or —$(C_1-C_3)$alkylene-phenylene-$(C_1-C_3)$alkylene-, where the phenylene is optionally substituted with 1, 2 or 3 substituents independently selected from $(C_1-C_6)$alkyl and halogen.

Embodiment 7. The biocompatible polymer pre-cure of any one of Embodiments 1 to 6, wherein the elastomeric backbone units (M), represented by the structural Formula (IVa): *—[—$A^1$-M-O—]—* (IVa), comprise recurring groups selected from the group consisting of —$(C_1-C_6)$alkylene-O—, —C(=O)—$(C_1-C_6)$alkylene-O—, —$(C_1-C_6)$alkylene-C(=O)O—, and —C(=O)O—$(C_1-C_6)$alkylene-O—, and any combinations thereof.

Embodiment 8. The biocompatible polymer pre-cure of any one of Embodiments 1 to 7, wherein the elastomeric backbone units (M) comprise recurring groups selected from the group consisting of

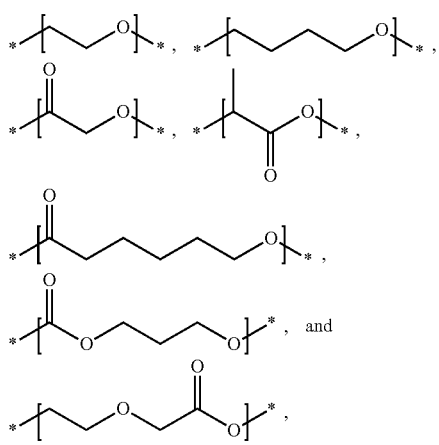

and any combinations thereof.

Embodiment 9. The biocompatible polymer pre-cure of any one of Embodiments 1 to 8, wherein the elastomeric backbone units (M) are derived from monomers selected from the group consisting of caprolactone, tetramethylene oxide, trimethylene carbonate, ethylene glycol, dioxanone, glycolide, and lactide; and M is selected form monomers, oligomers, homo-macromers, and any random or block co-macromers.

Embodiment 10. The biocompatible polymer pre-cure of any one of Embodiments 1 to 9, comprising:
the elastomeric backbone units (M), represented by structural Formula (IVa), *—[—$A^1$-M—]—* (IVa), at "c" wt %;
the non-elastomeric backbone units, comprising:
first recurring groups, represented by structural Formula (IIIa),

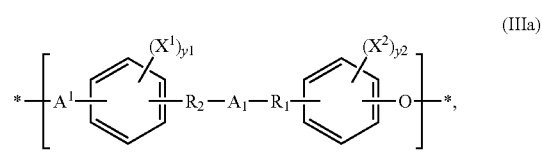

at "a" wt %; and
second recurring groups, represented by structural Formula (IIIb),

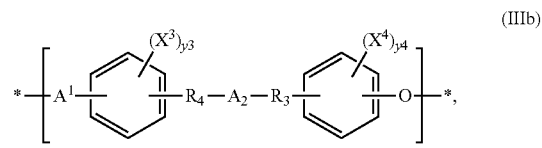

at "b" wt %;
wherein a+b+c=100%; and
wherein at least part of the crosslinkable pendant groups, in the latent or active form of structural Formula (Ia), (IIa) or (IIb), are attached to a carbon atom of the second recurring groups in the non-elastomeric backbone units.

Embodiment 11. The biocompatible polymer pre-cure of Embodiment 10, wherein:
$A^1$ is —C(=O)O—; and
the elastomeric backbone units (M) are represented by

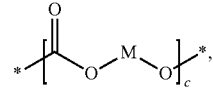

and are derived from monomers selected from the group consisting of caprolactone, tetramethylene oxide, trimethylene carbonate, ethylene glycol, dioxanone, glycolide, and lactide.

Embodiment 12. The biocompatible polymer pre-cure of Embodiment 11, wherein in the non-elastomeric backbone units:
the first recurring groups are selected from

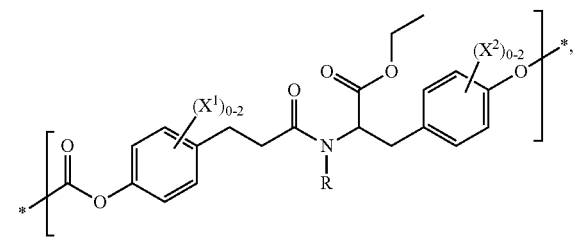

-continued and

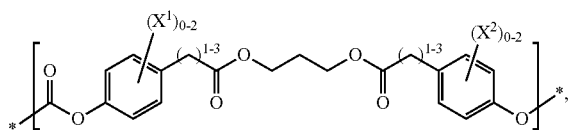

and any combinations thereof;

the second recurring groups, with the crosslinkable pendant groups attached, are selected from

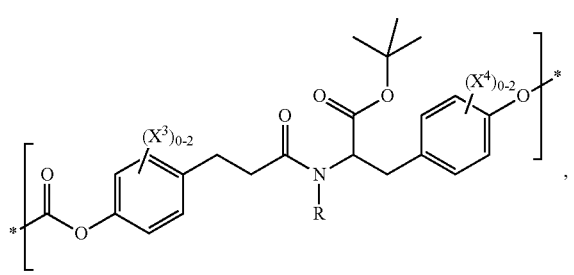
,

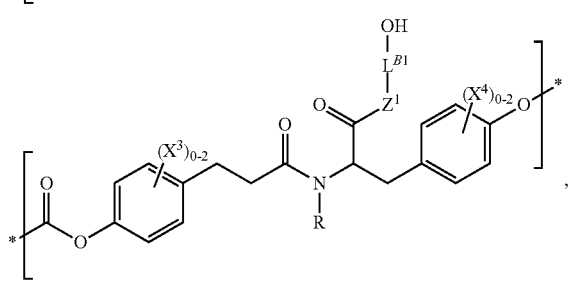
,

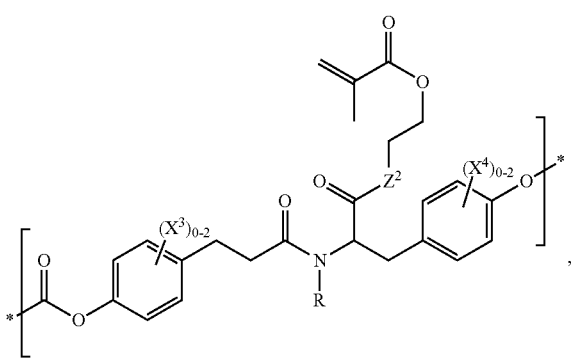
,

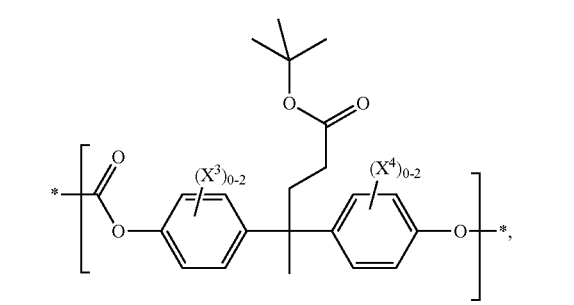
,

-continued

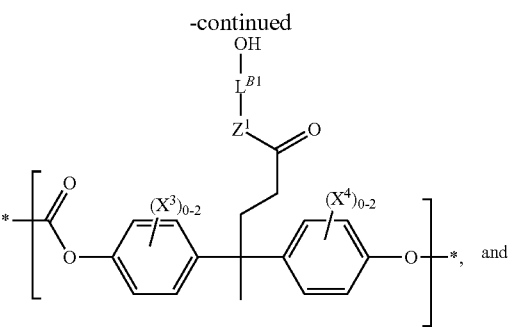
, and

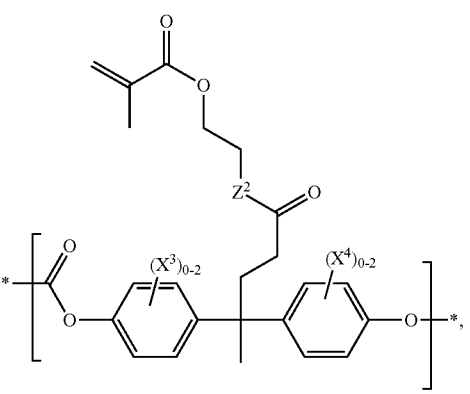
, and any combinations thereof, wherein:

R is H or $(C_1-C_6)$alkyl, such as methyl, ethyl, propyl, and butyl;

$Z^1$ and $Z^2$ are each independently O or NH; and $L^{B1}$ is $—(C_1-C_{10})$alkylene-, $—(C_1-C_{10})$alkenylene-, or $—(C_1-C_{10})$alkylene-phenylene-$(C_1-C_{10})$alkylene-, where the phenylene is optionally substituted with 1, 2 or 3 substituents independently selected from $(C_1-C_6)$ alkyl and halogen.

Embodiment 13. The biocompatible polymer pre-cure of Embodiment 12, wherein the cure treatment comprises heating and transesterification; and wherein in the non-elastomeric backbone units:

the first recurring groups are

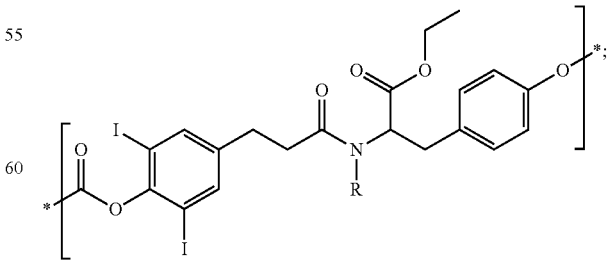

the second recurring groups, with the crosslinkable pendant groups attached, are

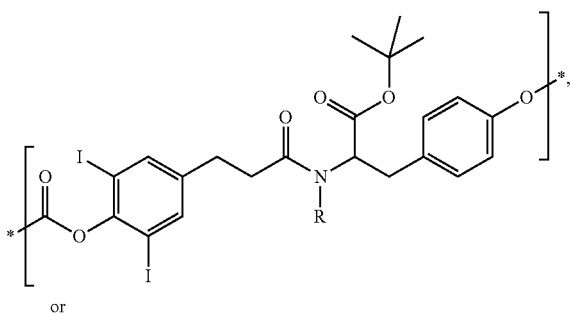

or

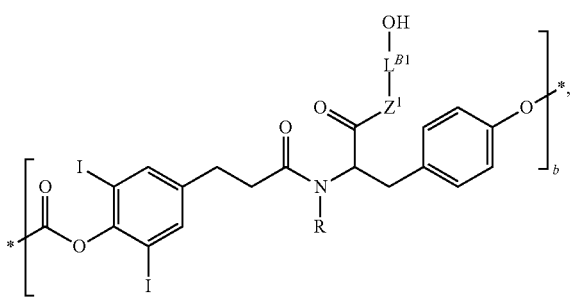

or any combination thereof.

Embodiment 14. The biocompatible polymer pre-cure of Embodiment 13, having a weight average molecular weight of about 50,000 to about 100,000, about 50,000 to about 300,000, about 50,000 to about 500,000, about 50,000 to about 700,000, or about 50,000 to about 1,000,000 g/mol.

Embodiment 15. The biocompatible polymer pre-cure of Embodiment 12, wherein the cure treatment comprises heating and transesterification; and wherein in the non-elastomeric backbone units:

the first recurring groups are

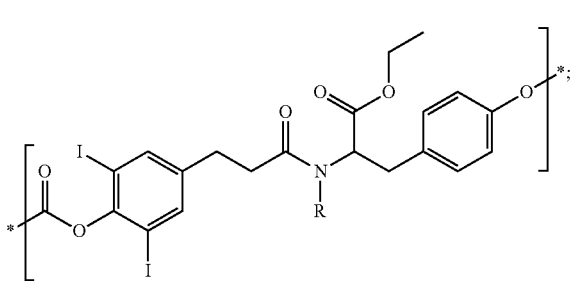

the second recurring groups, with the crosslinkable pendant groups attached, are

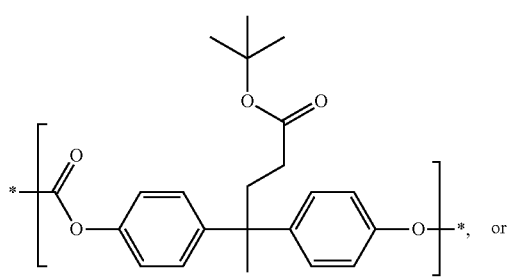, or

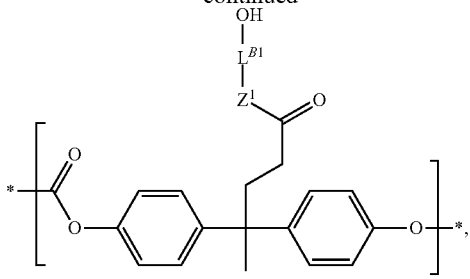

or any combination thereof.

Embodiment 16. The biocompatible polymer pre-cure of Embodiment 15, having a weight average molecular weight of about 50,000 to about 100,000, about 50,000 to about 300,000, about 50,000 to about 500,000, about 50,000 to about 700,000, or about 50,000 to about 1,000,000 g/mol.

Embodiment 17. The biocompatible polymer pre-cure of Embodiment 12, wherein the cure treatment comprises free-radical initiation; and wherein in the non-elastomeric backbone units:

the first recurring groups are

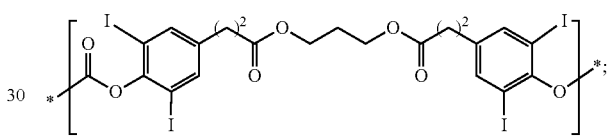

the second recurring groups, with the crosslinkable pendant groups attached, are

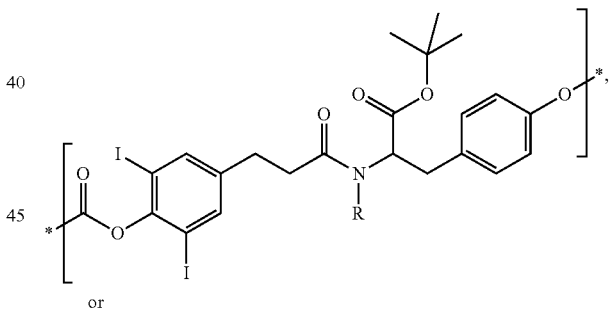

or

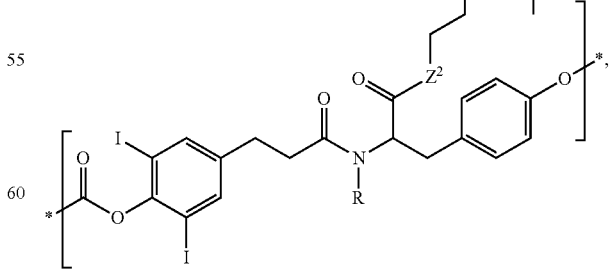

or any combination thereof.

Embodiment 18. The biocompatible polymer pre-cure of Embodiment 17, having a weight average molecular weight of about 50,000 to about 100,000, about 50,000 to about 300,000, about 50,000 to about 500,000, about 50,000 to about 700,000, or about 50,000 to about 1,000,000 g/mol.

Embodiment 19. The biocompatible polymer pre-cure of Embodiment 12, wherein the cure treatment comprises free-radical initiation; and wherein in the non-elastomeric backbone units:

the first recurring groups are

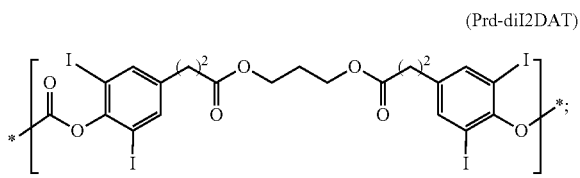
(Prd-diI2DAT)

the second recurring groups, with the crosslinkable pendant groups attached, are

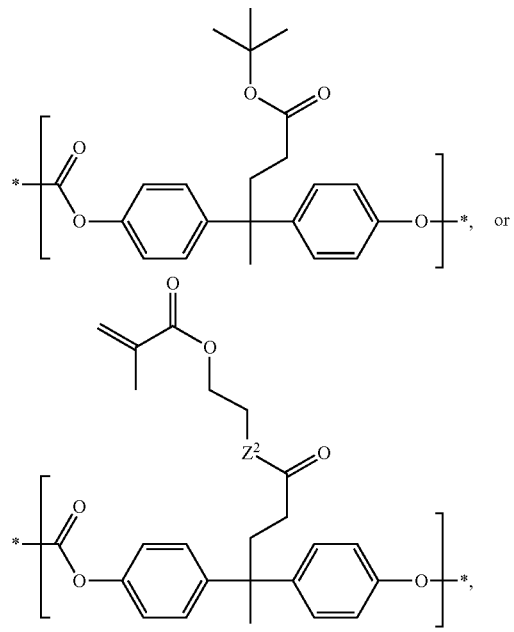

or any combination thereof.

Embodiment 20. The biocompatible polymer pre-cure of Embodiment 19, having a weight average molecular weight of about 50,000 to about 100,000, about 50,000 to about 300,000, about 50,000 to about 500,000, about 50,000 to about 700,000, or about 50,000 to about 1,000,000 g/mol.

Embodiment 21. The biocompatible polymer pre-cure of any one of Embodiments 1 to 20, wherein at least part of the latent form of the crosslinkable pendant groups, represented by structural Formula (I), are attached to the elastomeric backbone units.

Embodiment 22. The biocompatible polymer pre-cure of any one of Embodiments 1 to 20, wherein at least part of the active form of the crosslinkable pendant groups, represented by structural Formula (IIa) or (IIb), are attached to the elastomeric backbone units.

Embodiment 23. The biocompatible polymer pre-cure of Embodiment 22, wherein the elastomeric backbone units (M) comprise one or more of

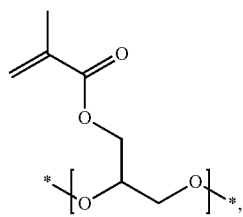

Embodiment 24. The biocompatible polymer pre-cure of Embodiment 23, wherein the elastomeric backbone units (M) comprise co-macromers derived from glycerol monomethacrylate and trimethyl carbonate.

Embodiment 25. The biocompatible polymer pre-cure of Embodiment 22 or 23, comprising:

"c" wt % of the elastomeric backbone units (M), comprising co-macromers represented by

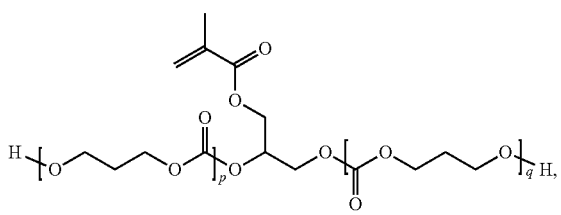

where p and q are each independently an integer of 0 to 50;

"a" wt % of the first recurring groups:

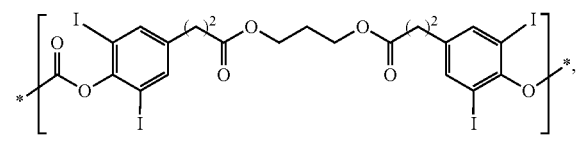

in the non-elastomeric backbone units; and

"b" wt % of the second recurring groups, with the crosslinkable pendant groups attached, in the non-elastomeric backbone units;

the second recurring groups are

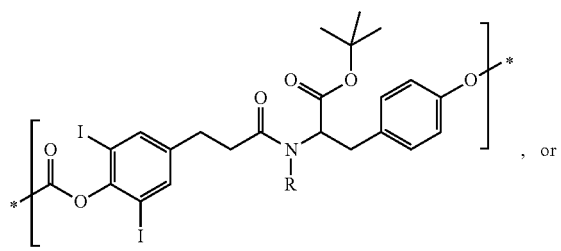
, or

-continued

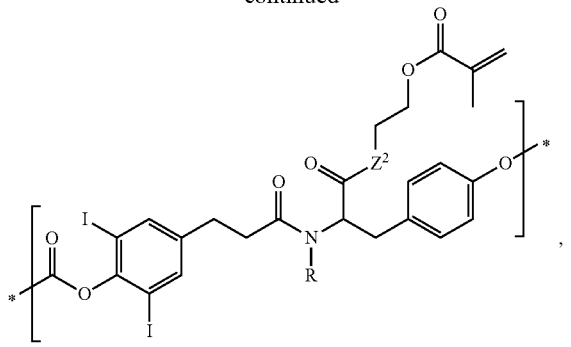

or any combination thereof;
each of a %, b %, and c %, if the respective recurring unit is present, independently ranges between about 1% to about 5%, about 1% to about 10%, about 1% to about 15%, about 1% to about 20%, about 1% to about 25%, about 1% to about 30%, about 1% to about 35%, about 1% to about 40%, about 1% to about 45%, about 1% to about 50%, about 5% to about 10%, about 5% to about 15%, about 5% to about 20%, about 5% to about 25%, about 5% to about 30%, about 5% to about 35%, about 5% to about 40%, about 5% to about 45%, or about 5% to about 50% by weight of the biocompatible polymer pre-cure; and $a+b+c=100\%$.

Embodiment 26. The biocompatible polymer pre-cure of Embodiment 25, having a weight average molecular weight of about 50,000 to about 100,000, about 50,000 to about 300,000, about 50,000 to about 500,000, about 50,000 to about 700,000, or about 50,000 to about 1,000,000 g/mol.

Embodiment 27. The biocompatible polymer pre-cure of any one of Embodiments 1 to 26, wherein the configuration is a medical device, or a medical implant, or a part thereof.

Embodiment 28. The biocompatible polymer pre-cure of Embodiment 27, wherein the configuration is a vascular scaffold.

Embodiment 29. The biocompatible polymer pre-cure of Embodiment 27 or 28, wherein the configuration is tubular.

Embodiment 30. The biocompatible polymer pre-cure of any one of Embodiments 27 to 29, wherein the configuration is a stent or stent-graft.

Embodiment 31. The biocompatible polymer pre-cure of any one of Embodiments 1 to 30 is configured to be laser-cut in the configuration.

Embodiment 32. A biocompatible polymer post-cure of any one of Embodiments 1 to 31, wherein the cure treatment comprises heating, transesterification, free-radical initiation, or a combination thereof.

Embodiment 33. The biocompatible polymer post-cure of Embodiment 32, comprising a crosslinking density of about 1%, about 5%, about 10%, about 20%, about 30%, about 40%, about 50%, about 60%, about 70%, about 80%, about 90%, or about 95%.

Embodiment 34. The biocompatible polymer post-cure of Embodiment 32 or 33 is inherently radiopaque.

Embodiment 35. The biocompatible polymer post-cure of any one of Embodiments 32 to 34 is bioresorbable.

Embodiment 36. The biocompatible polymer post-cure of any one of Embodiments 32 to 35 is configured to be laser-cut.

Embodiment 37. A polymer material, comprising a biocompatible polymer pre-cure of any one of Embodiments 1 to 31, or a biocompatible polymer post-cure of any one of Embodiments 32 to 36.

Embodiment 38. A medical device, comprising a biocompatible polymer pre-cure of any one of Embodiments 1 to 31, or a biocompatible polymer post-cure of any one of Embodiments 32 to 36.

Embodiment 39. A method of preparing a biocompatible polymer post-cure of any one of Embodiments 32 to 36, comprising:
preparing a biocompatible polymer pre-cure of any one of Embodiments 1 to 31;
activating the latent form of the crosslinkable pendant groups via the activation treatment; and
crosslinking the active form of the crosslinkable pendant groups via the cure treatment.

Embodiment 40. The method of Embodiment 39, wherein the activating step is carried out prior to, substantially simultaneously with, the crosslinking step.

Embodiment 41. The method of Embodiment 39 or 40, comprising, in any order, one or more activating steps and one or more crosslinking steps.

Embodiment 42. The method of any one of Embodiments 39 to 41, further comprising allowing the biocompatible polymer pre-cure to form the configuration.

Embodiment 43. The method of Embodiment 42, further comprising modifying the configuration, such as by laser-cutting, to form a vascular scaffold device or a part thereof.

Embodiment 44. A method of making a polymer material or a medical device, comprising a biocompatible polymer post-cure of any one of Embodiments 32 to 36, comprising:
preparing a biocompatible polymer pre-cure of any one of Embodiments 1 to 31;
activating the latent form of the crosslinkable pendant groups via the activation treatment; and
crosslinking the active form of the crosslinkable pendant groups via the cure treatment;
wherein the biocompatible polymer post-cure is bioresorbable and inherently radiopaque.

Embodiment 45. The method of Embodiment 44, wherein the activating step is carried out prior to, substantially simultaneously with, the crosslinking step.

Embodiment 46. The method of Embodiment 44 or 45, comprising, in any order, one or more activating steps and one or more crosslinking steps.

Embodiment 47. The method of any one of Embodiments 45 to 56 further comprises allowing the biocompatible polymer pre-cure to assume a configuration, prior to, substantially simultaneously with, any one of the activating step.

Embodiment 48. The method of Embodiment 47 further comprises modifying the configuration, such as by laser-cutting, prior to, substantially simultaneously with, or subsequent to any one of the crosslinking step, to form a vascular scaffold device or a part thereof.

Embodiment 49. The method of any one of Embodiments 44 to 48 further comprises determining one or more mechanical properties of the biocompatible polymer pre-cure or post-cure, wherein the one or more mechanical properties are selected from the group consisting of toughness, resilience, impact resistance, and crush recovery, and any combinations thereof.

Embodiment 50. A polymer material made using any combinations of all or part of the steps of the method of any one of Embodiments 44 to 49.

Embodiment 51. A medical device comprising a polymer material made using any combinations of all or part of the steps of the method of any one of Embodiments 44 to 49.

Embodiment 52. The medical device of Embodiment 38 or 51 is a vascular scaffold, such as a stent or stent-graft.

Embodiment 53. The polymer material of Embodiment 37 or 50, or the medical device of any one of Embodiments 38 and 51-52, wherein the configuration is tubular.

Embodiment 54. The polymer material of Embodiment 41 or 55, or the medical device of any one of Embodiments 38 and 51-52, is tough, resilient, impact resistant, crush recoverable, or a combination thereof.

Embodiment 55. The polymer material of Embodiment 41 or 55, or the medical device of any one of Embodiments 38 and 51-52, further comprises a coating, wherein the coating comprises a pharmaceutical agent, or a drug, or both.

Embodiment 61. A biocompatible polymer precure of any one of the preceding Embodiments is a homopolymer, a random copolymer, a block copolymer, or any combination thereof.

2. The polymer material of claim 1, wherein the material is in a latently cross-linkable state, the material not having been subjected to the at least one initiation treatment.

3. The polymer material of claim 1, wherein the material is in a cross-linked state, the material having been subjected to the at least one initiation treatment.

4. The polymer material of claim 1, wherein the at least one polymer component which as initially prepared has a rubbery or partially rubber state, comprises one or more of PCL (polycaprolactone), PTMO (polytetramethylene oxide), PTMC (polytrimethylene carbonate), PEG (polyethylene glycol), polydioxanone, polyglycolide, polylactide, and any co-macromers thereof.

5. The polymer material of claim 1, wherein the at least one polymer component which has a latently cross-linkable polymer material comprises an inherently radiopaque, biocompatible, bioresorbable polymer, wherein the polymer comprises one or more of the recurring units having the following structures:

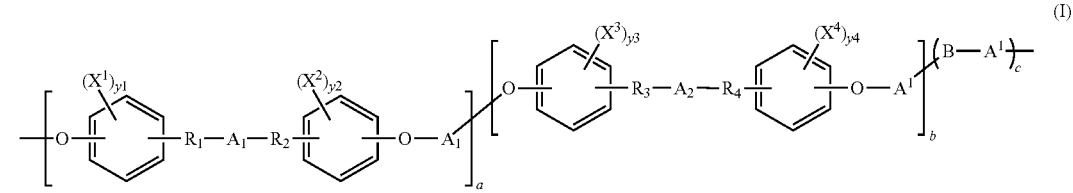

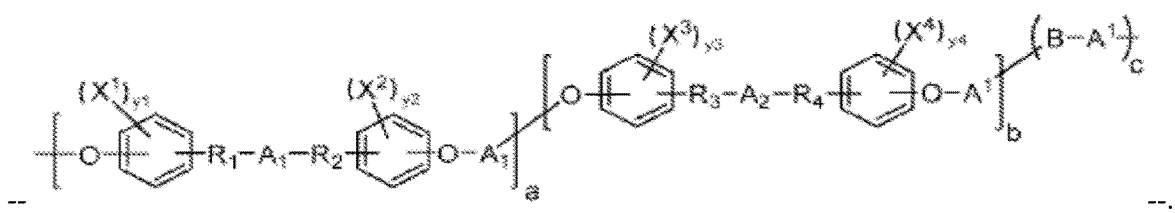
Column 63-64, Lines 40-65 (approx.), Claim 29, delete
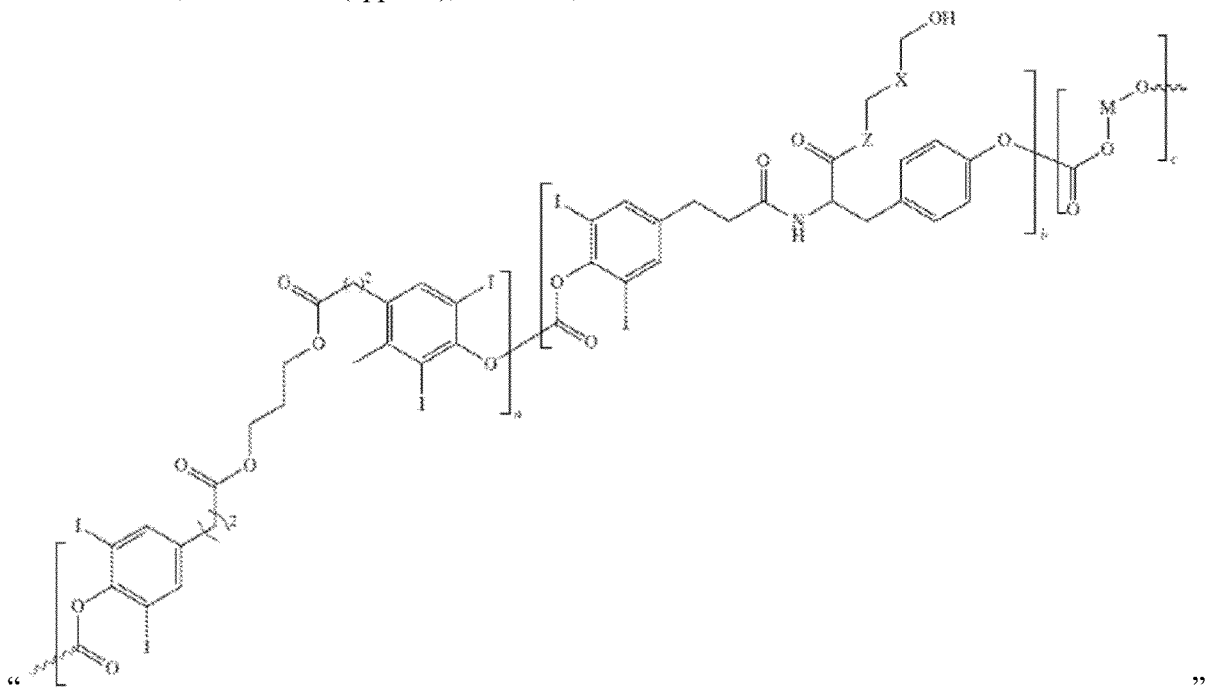
"
and insert
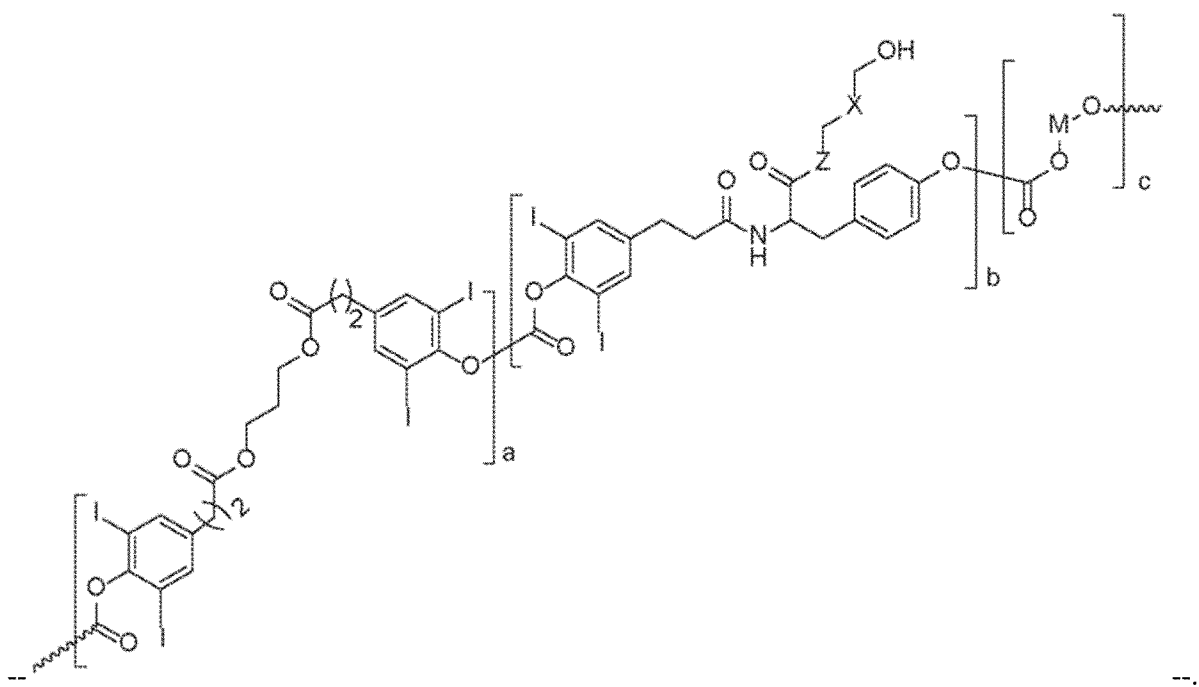

What is claimed is:

1. A polymer material, comprising one or more of polymers, homogeneous polymers, copolymers, block co-polymers, and/or blends or mixtures thereof; wherein the biocompatible polymer material is optionally inherently radiopaque, and/or bioresorbable;
   wherein the polymer material comprises at least one polymer component which, as initially prepared, has a latently cross-linkable state, such that it comprises functional groups which are configured to react upon being subjected to at least one cross-linking initiation treatment to crosslink the polymer;
   wherein the polymer material comprises at least one polymer component which, as initially prepared, has a rubbery or partially rubber state at a temperature less than 37° C.;
   wherein the polymer material, prior to being subjected to the at least one cross-linking initiation treatment, has properties allowing it to be formed into a selected structural shape without initiating cross-linking; and
   wherein the polymer material, after subjected to at least one cross-linking initiation treatment, has a cross-linked state, such that it has a sufficient number and/or density of cross-links between polymer chains within the material so as to enhance the material properties to create a strong, tough, resilient material, such that a selected shape composed of the cross-linked polymer material has crush-recoverable properties allowing substantial return to the selected shape following mechanical deformation.

wherein
   each of "a," "b," "c", if the respective recurring unit is present, independently ranges between about 1% to about 5%, about 1% to about 10%, about 1% to about 15%, about 1% to about 20%, about 1% to about 25%, about 1% to about 30%, about 1% to about 35%, about 1% to about 40%, about 1% to about 45%, about 1% to about 50%, about 5% to about 10%, about 5% to about 15%, about 5% to about 20%, about 5% to about 25%, about 5% to about 30%, about 5% to about 35%, about 5% to about 40%, about 5% to about 45%, or about 5% to about 50% by weight of the polymer;
   the polymer is a random or block co-polymer;
   each of $X^1$, $X^2$, $X^3$ and $X^4$ is independently Br or I;
   each of y1, y2, y3 and y4 is independently 0, 1, 2, 3 or 4;
   a, b, and c are weight percentages range from 0 to 100% and a+b+c=100%; and
   $A_1$, $A_2$ and $A^1$ are linking groups independently selected from the group consisting of:

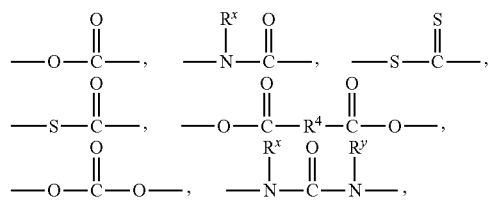

-continued

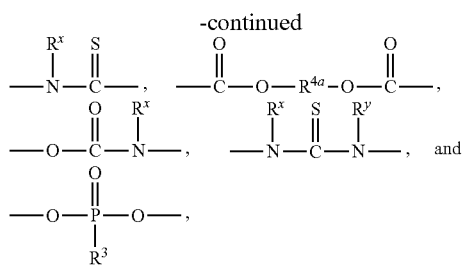

with the proviso that in the event an oxygen-oxygen or oxygen-nitrogen bond is implied by the linking of the $A_1$, $A_2$ or $A^1$ to a neighboring oxygen atom, then that neighboring oxygen atom is absent;

B is the at least one polymer component which as initially prepared has a rubbery or partially rubbery state;

each of $R^x$, $R^y$, $R^3$ is independently H or $C_1$-$C_6$ alkyl;

each of $R^4$ and $R^{4a}$ is independently $C_1$-$C_{10}$ alkylene;

each of $R_1$, $R_2$, $R_3$ and $R_4$ is independently straight-chain or branched, saturated or unsaturated $C_1$-$C_{12}$ alkylene, 2-15 membered heteroalkylene, or 2-15 membered heteroalkenylene, each optionally comprising 1-3 heteroatoms each independently selected from O, NR, and S;

R is H or $C_1$-$C_6$ alkyl;

each of $R_1$, $R_2$, $R_3$ and $R_4$ optionally comprise a pendant Z group; and the pendant Z group optionally comprises functional groups that can react to crosslink the polymer, after it is fabricated into a desired shape, by either an elimination reaction or by a free radical mechanism.

6. The polymer material of claim 1, wherein the polymer material comprises a polymer including one or more of the recurring units having the following structure:

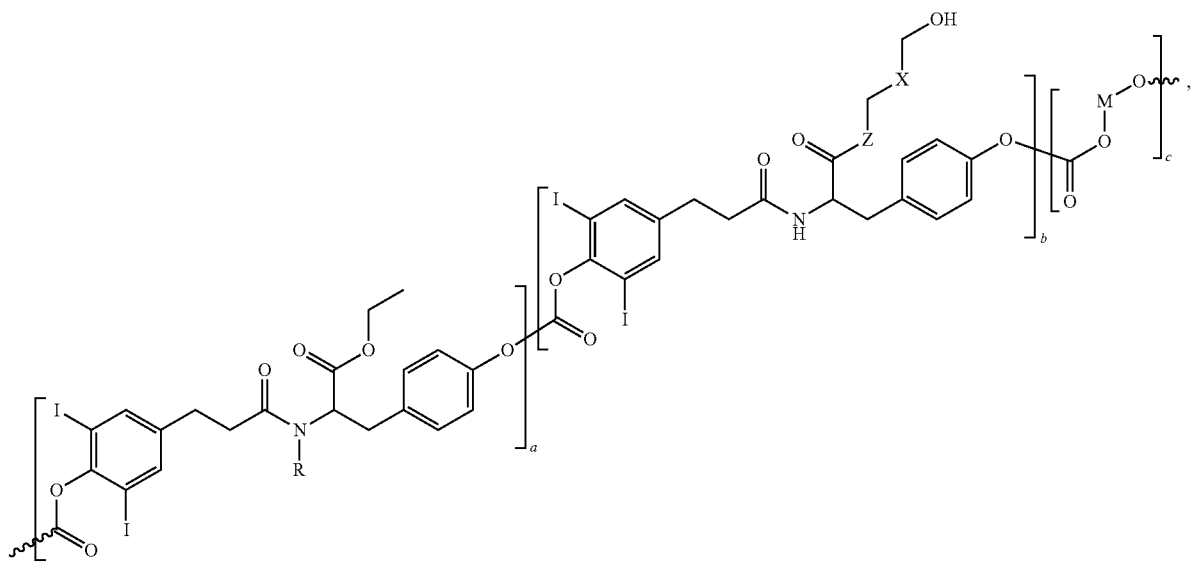

(II)

wherein:

M is a low Tg macromer, comprising PTMC, PTMO, PCL, PEG, or any co-macromers thereof, optionally further comprising one or more of PLLA, PGA, and polydioxane;

Z=O or NH; and

X is a bond or a straight chain or branched alkylene, alkenylene, or phenylene, each optionally substituted with one or more substituents selected from alkyl, halogen, —OH, and —C(O)OH; and the polymer is a random or block co-polymer;

wherein the at least one cross-linking initiation treatment comprises heating the latently cross-linkable polymer material to induce transesterification.

7. The polymer material of claim 1, wherein the polymer material comprises a polymer including one or more of the recurring units having the following structure:

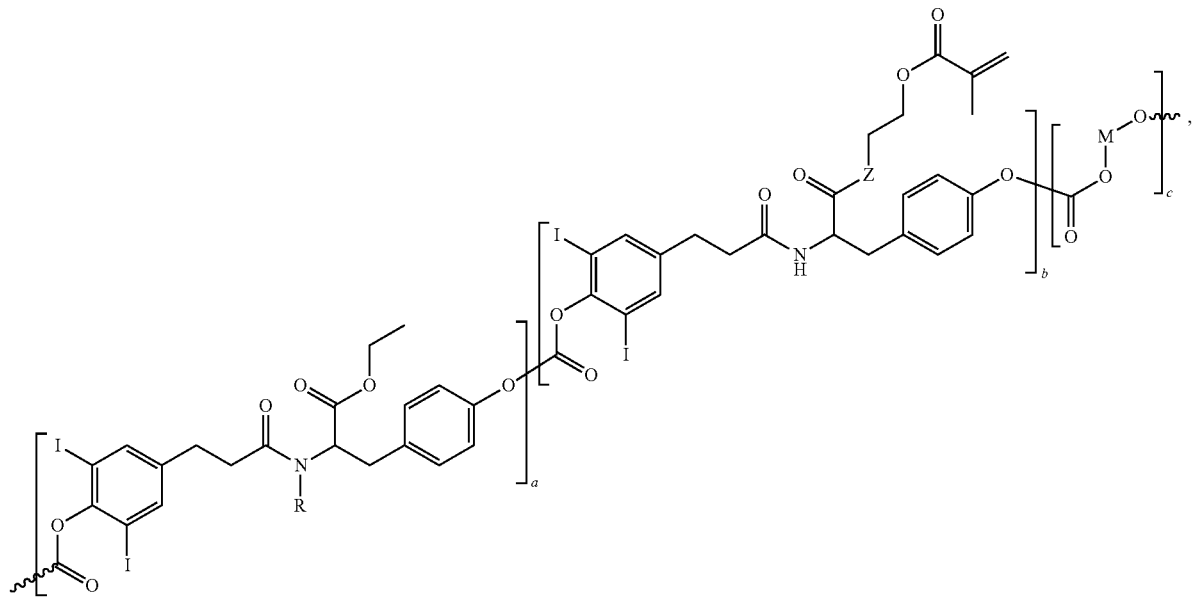

(III)

wherein:
M is a low Tg macromer, comprising PTMC, PTMO, PCL, PEG, or any co-macromers thereof, optionally further comprising one or more of PLLA, PGA, and polydioxane; and
Z=O or NH; and
the polymer is a random or block co-polymer;

wherein the at least one cross-linking initiation treatment comprises a free radical initiated chain reaction of polymer in the presence of free radical initiator.

8. The polymer material of claim 1, wherein the polymer material comprises a polymer including one or more of the recurring units having the following structures:

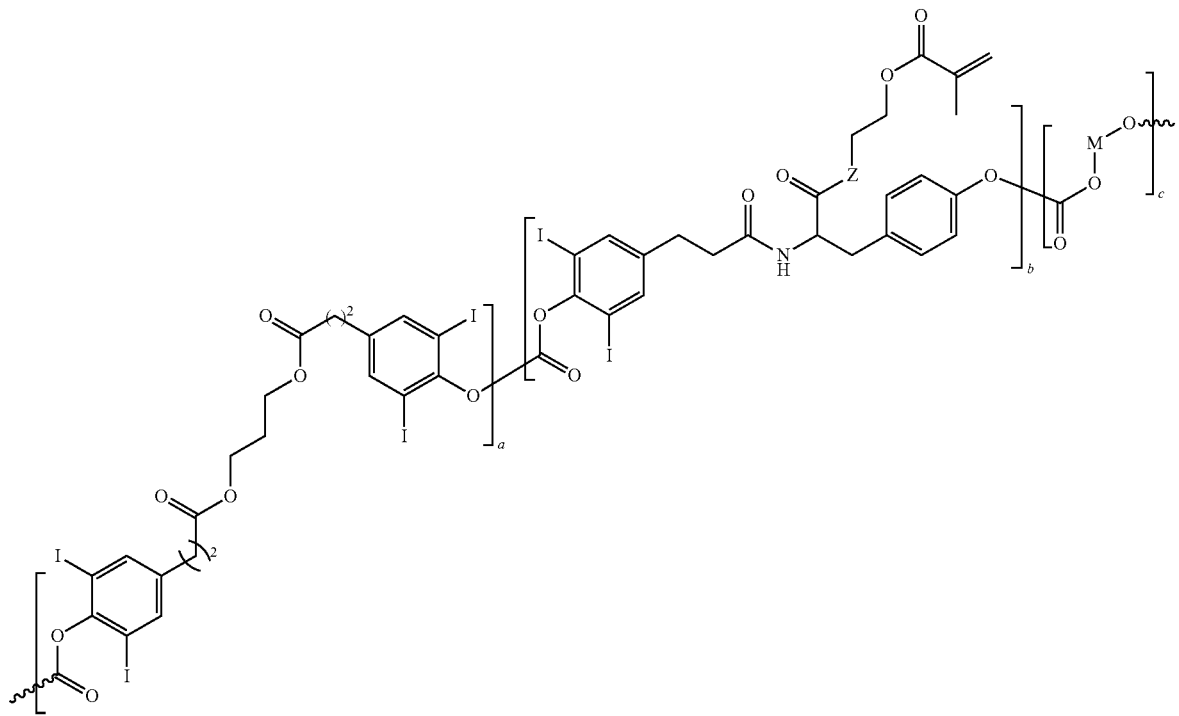

(VI)

wherein M is a low Tg macromer, comprising PTMC, PTMO, PCL, PEG, or any co-macromers thereof, optionally further comprising one or more of PLLA, PGA, and polydioxane; and Z=O or NH; and wherein the at least one cross-linking initiation treatment comprises a free radical initiated chain reaction of polymer in the presence of free radical initiator.

9. The polymer material of claim 6 wherein the moiety in brackets "b" is replaced by a t-butyl ester of diphenolic acid according to the following structures:

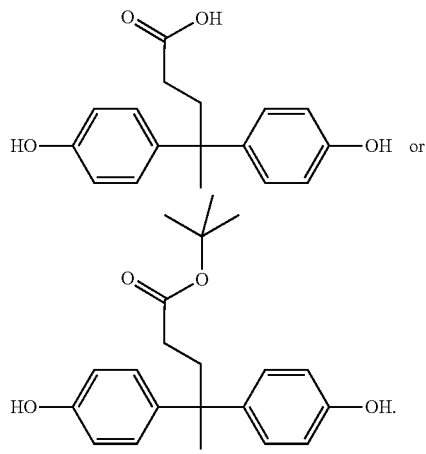

10. The polymer material of claim 6, wherein R=H.

11. The polymer material of claim 6, wherein R is a straight chain or branched chain alkyl group.

12. The polymer material of claim 6, wherein R is $CH_3$ or $C_2H_5$.

13. The polymer material of claim 1, wherein the polymer material comprises a polymer including one or more of the recurring units having the following structure, when cross-linking functional group is in the side chain of an inherently rubbery PTMC:

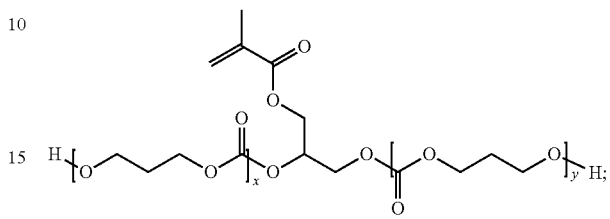

wherein each of x and y is independently an integer in the range of about 1 to about 50.

14. The polymer material of claim 1, wherein the polymer material comprises a polymer including at least two distinct kinds of the recurring units, each such kind of recurring unit having a different type of the latently crosslinkable functional groups; and wherein one such recurring unit is a structural radiopaque component including a crosslinkable acryloyl or methacryloyl moiety in the pendant group; and wherein another such recurring unit is an inherently rubbery component including a crosslinkable acryloyl or methacryloyl moiety in the pendant group.

15. The polymer material of claim 13, wherein the polymer material comprises a polymer including one or more of the recurring units having the following structure:

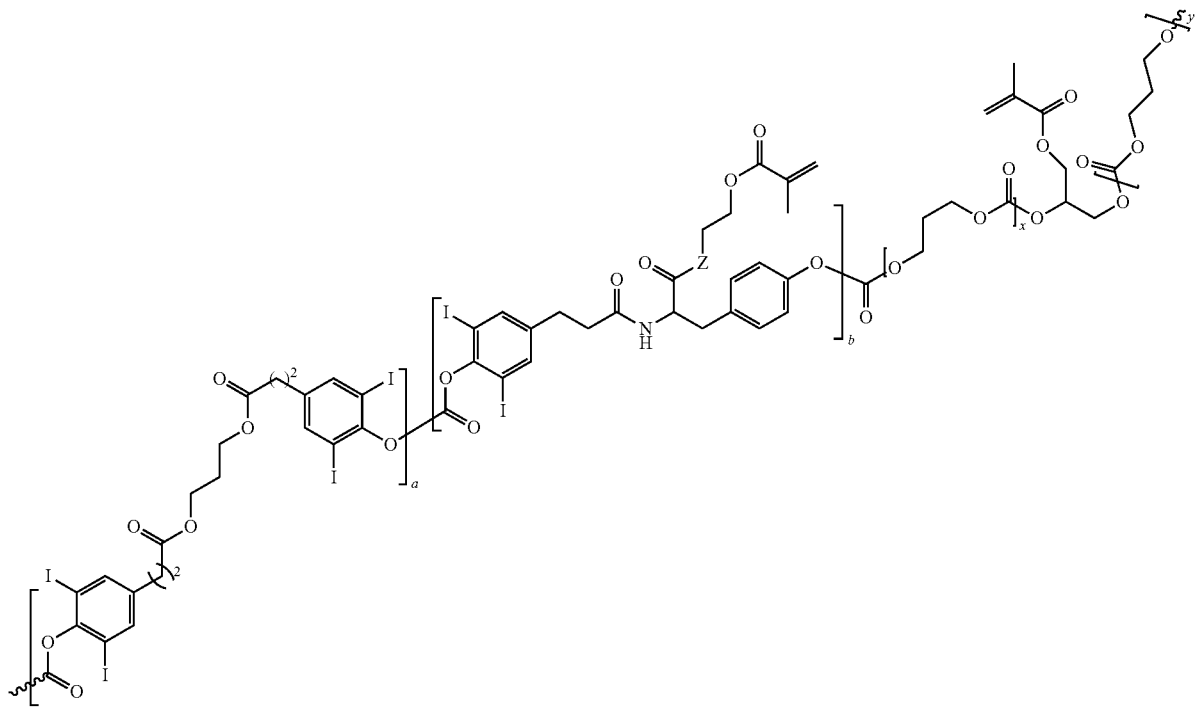

wherein Z is O, S or NH.

16. A medical device comprising at least one structural portion;
   wherein the structural portion has been previously formed from a latently cross-linkable polymer material to have a pre-formed shape, the latently cross-linkable polymer material including one or more polymers or copolymers which are inherently radiopaque, biocompatible, and/or bioresorbable;
   wherein, subsequent to the formation of the pre-formed shape of the structural portion, the latently cross-linkable polymer material of the structural portion has been subjected to at least one cross-linking initiation treatment so as to form a sufficient number and/or density of cross-links between polymer chains within the material so as to enhance the material properties to create a strong, tough, resilient, and/or crush-recoverable material having the pre-formed shape; and
   wherein optionally the cross-linked pre-form shape is further fabricated to making the medical device.

17. The medical device of claim 16, wherein the latently cross-linkable polymer material comprises an inherently radiopaque, biocompatible, bioresorbable polymer, wherein the polymer comprises one or more of the recurring units having the following structure:

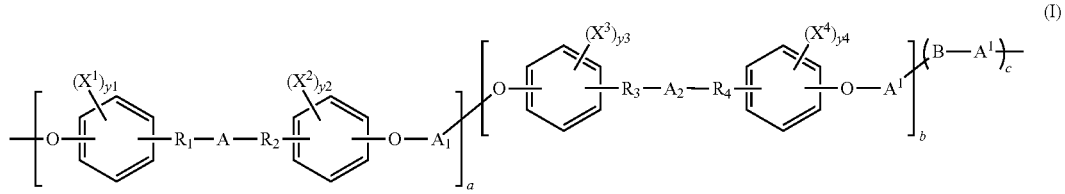

wherein
   each of "a," "b," "c", if the respective recurring unit is present, independently ranges between about 1% to about 5%, about 1% to about 10%, about 1% to about 15%, about 1% to about 20%, about 1% to about 25%, about 1% to about 30%, about 1% to about 35%, about 1% to about 40%, about 1% to about 45%, about 1% to about 50%, about 5% to about 10%, about 5% to about 15%, about 5% to about 20%, about 5% to about 25%, about 5% to about 30%, about 5% to about 35%, about 5% to about 40%, about 5% to about 45%, or about 5% to about 50% by weight of the polymer;
   the polymer is a random or block co-polymer;
   each of $X^1$, $X^2$, $X^3$ and $X^4$ is independently Br or I;
   each of y1, y2, y3 and y4 is independently 0, 1, 2, 3, or 4;
   a, b, and c are weight percentages range from 0 to 100% and a+b+c=100%; $A_1$, $A_2$ and $A^1$ are linking groups independently selected from

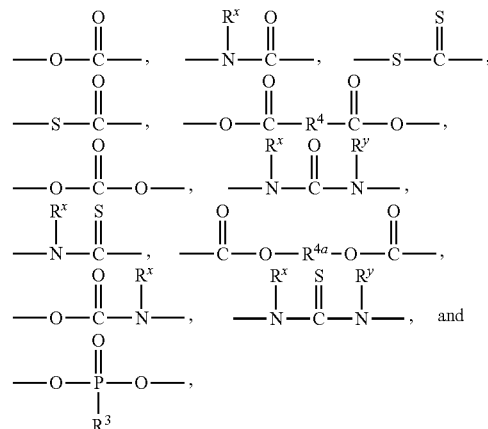

with the proviso that in the event an oxygen-oxygen or oxygen-nitrogen bond is implied by the linking of the $A_1$, $A_2$ or $A^1$ to a neighboring oxygen atom, then that neighboring oxygen atom is absent;
   B is the at least one polymer component which as initially prepared has a rubbery or partially rubber state;
   each of $R^x$, $R^y$, $R^3$ is independently H or $C_1$-$C_6$ alkyl;
   each of $R^4$ and $R^{4a}$ is independently $C_1$-$C_{10}$ alkylene;
   each of $R_1$, $R_2$, $R_3$ and $R_4$ is independently a straight-chain or branched, saturated or unsaturated $C_1$-$C_{12}$ alkylene, 2-15 membered heteroalkylene, or 2-15 membered hetero-($C_1$-$C_{12}$)alkenylene, each optionally comprising 1-3 heteroatoms each independently selected from O, NR, and S;
   R is H or $C_1$-$C_6$ alkyl,
   each of $R_1$, $R_2$, $R_3$ and $R_4$ optionally comprising a pendant Z group and;
   the pendant Z group optionally comprises functional groups that can react to crosslink the polymer, after it is fabricated into a desired shape, by either an elimination reaction or by a free radical mechanism.

18. The medical device of claim 16, wherein the latently cross-linkable polymer material comprises the following structure:

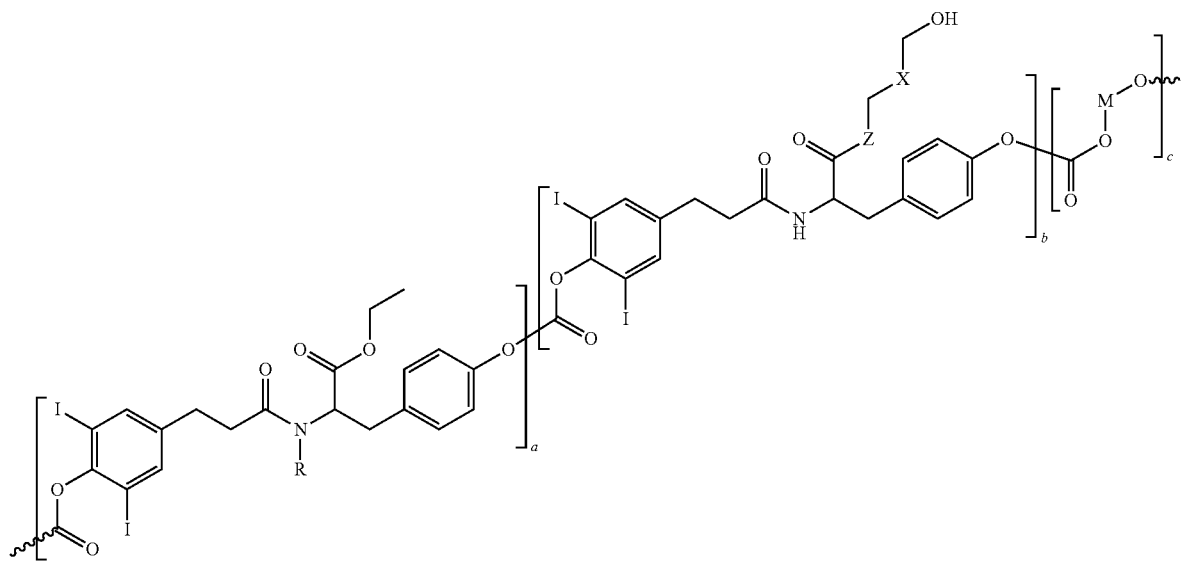

(II)

wherein
M comprises a low Tg macromer, further comprising PTMC, PTMO, PCL, PEG, PLLA, PGA, polydioxane, or any co-macromers thereof;
Z=O or NH; and
X is a straight chain or branched alkylene, alkenylene, or substituted or unsubstituted phenylene, wherein the at least one cross-linking initiation treatment comprises heating the latently cross-linkable polymer material to induce transesterification.

19. The medical device of claim 16, wherein the latently cross-linkable polymer material comprises the following structure:

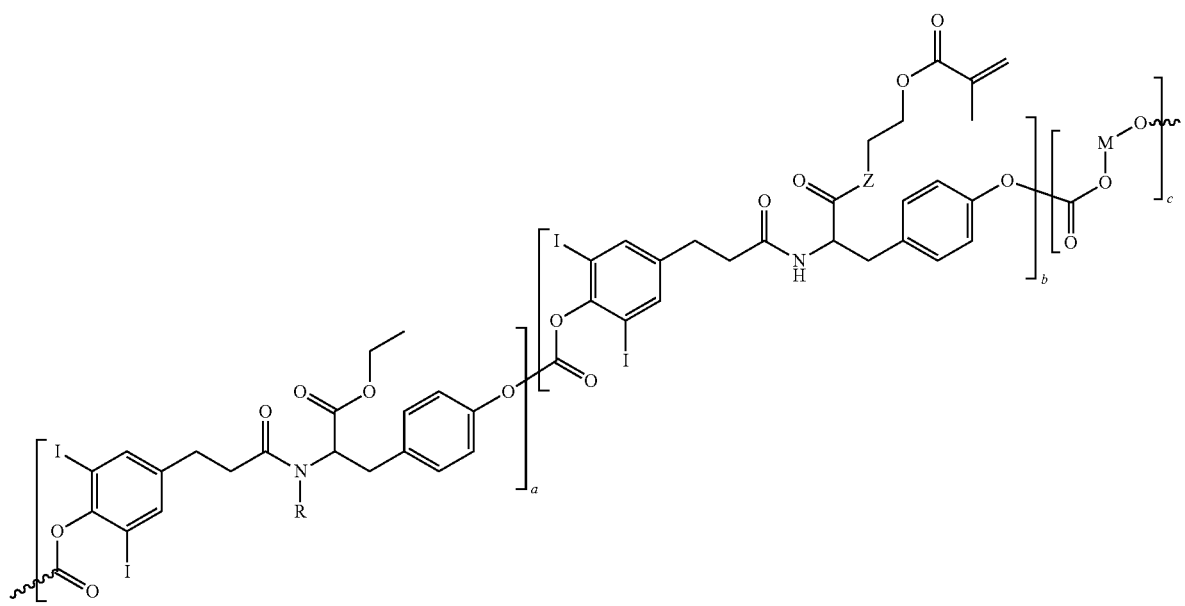

(III)

wherein
M comprises a low Tg macromer, further comprising PTMC, PTMO, PCL, PLLA, PGA, polydioxane, or any co-macromers thereof; and
Z=O or NH; and
wherein the at least one cross-linking initiation treatment comprises a free radical initiated chain reaction of polymer in the presence of free radical initiator.

20. The medical device of claim 16, wherein the latently cross-linkable polymer material comprises the following structure:

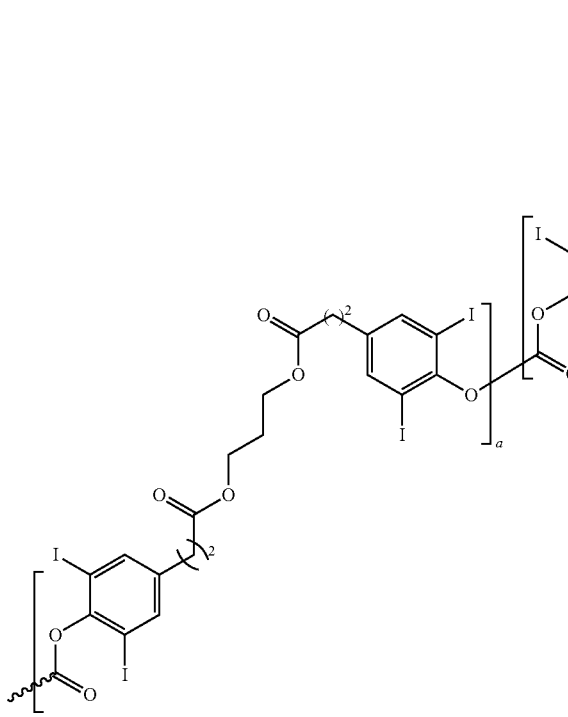

21. The medical device of claim 16, wherein the pre-formed shape of the structural portion is tubular.

22. The medical device of claim 21, wherein the tubular pre-formed shape of the structural portion is laser-cut to form at least a portion of a vascular scaffold device, the laser cutting being either prior to or subsequent to cross-linking of the polymer material.

23. A method of making a medical device having a structure comprising an inherently radiopaque, biocompatible, and/or bioresorbable polymeric material, the structure having at least one of the properties of toughness, resiliency, impact-resistance and/or crush recoverability upon deformation, the method comprising, in any functional order, the steps of:
   (a) preparing a latently cross-linkable polymer material which comprises polymer or copolymer which is inherently radiopaque, biocompatible and/or bioresorbable, and which is capable of subsequently forming cross-links between polymer chains upon being subjected to at least one cross-linking initiation treatment;
   (b) forming at least one pre-formed structural shape portion, the pre-formed structural shape portion including the latently cross-linkable polymer material;
   (c) after forming step (b), subjecting the pre-formed structural shape portion to at least one cross-linking initiation treatment so as to forming cross-links between polymer chains, resulting in the formation of a cross-linked structural shape portion having at least one of the properties of toughness, resiliency, impact-resistance and/or crush recoverability upon deformation;
   (d) after treatment step (c), optionally carrying out forming, treating and/or conditioning steps to modify the cross-linked structural shape portion;
   (e) making the medical device so as to comprise the cross-linked structural shape portion.

24. A medical device made using all or a portion of the steps, in any order, of the method of claim 23.

25. The medical device of claim 24, wherein the device comprises a vascular scaffold.

26. The medical device of claim 16, wherein the device comprises a polymer including one or more of the recurring units having the following structure:

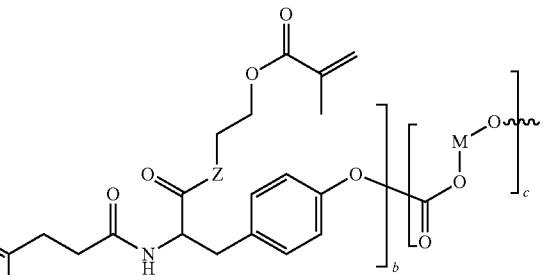

wherein:
   each of x and y is independently an integer in the range of about 1 to about 50.

27. The medical device of claim 16, wherein the device comprises a polymer including one or more of the recurring units having the following structure:

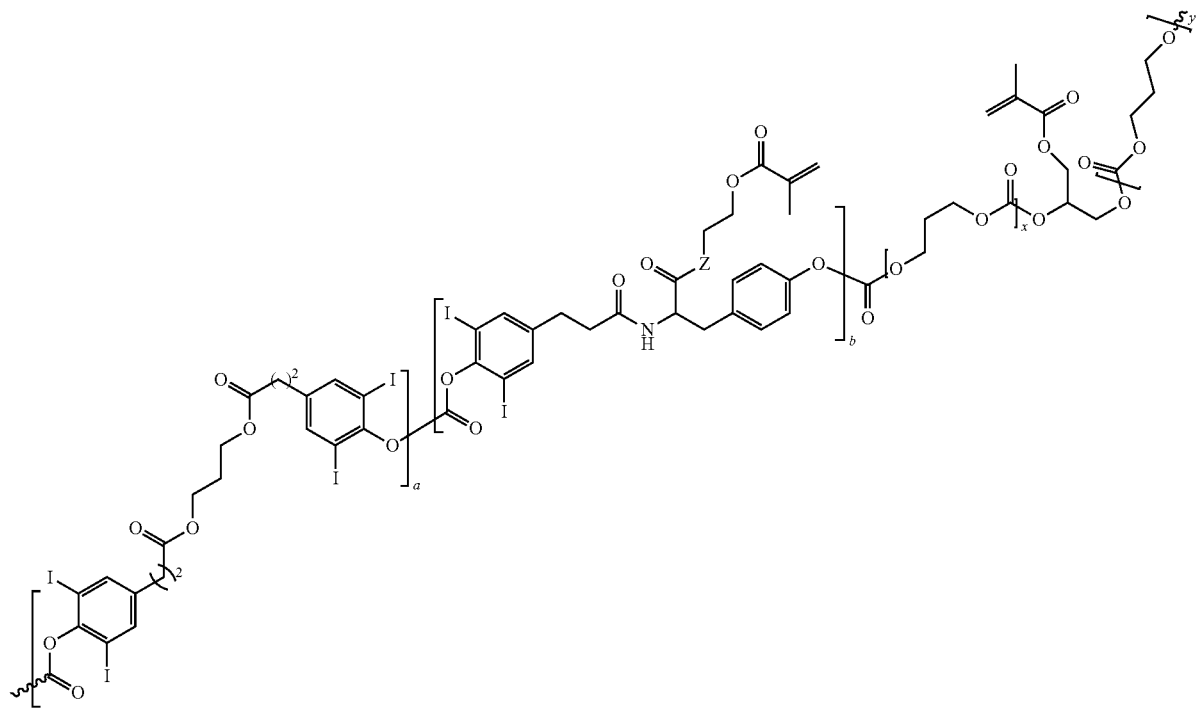

wherein Z is O, S or NH.

28. The medical device of claim 16, wherein the device comprises a coating including a drug and/or pharmaceutic agent.

29. The polymer material of claim 1, wherein the polymer material comprises a polymer including one or more of the recurring units having the following structures:

wherein M is a low Tg macromer, comprising PTMC, PTMO, PCL, PEG, or any co-macromers thereof, optionally further comprising one or more of PLLA, PGA, and polydioxane; and Z=O or NH; and X is a bond or a straight chain or branched alkylene, alkenylene, or phenylene, each optionally substituted

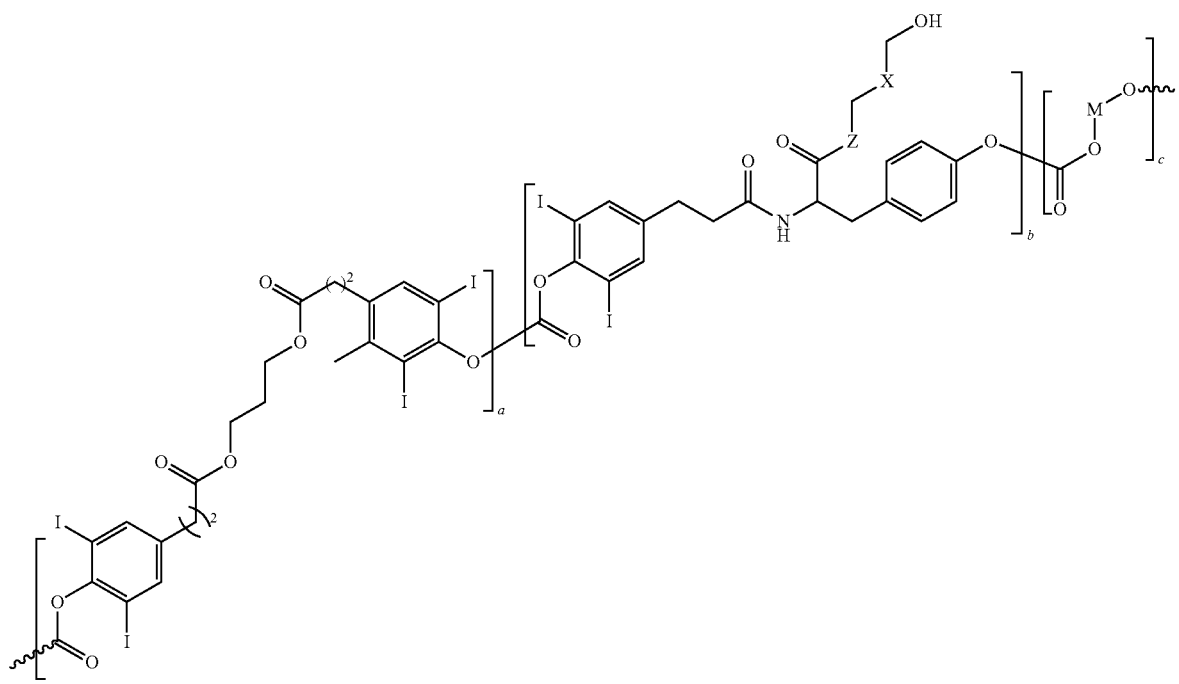

with one or more substituents selected from alkyl, halogen, —OH, and —C(O)OH; and the polymer is a random or block co-polymer;

wherein the at least one cross-linking initiation treatment comprises heating the latently cross-linkable polymer material to induce transesterification.

30. A medical device comprising the polymer material of claim 29.

* * * * *

UNITED STATES PATENT AND TRADEMARK OFFICE
CERTIFICATE OF CORRECTION

PATENT NO. : 12,012,483 B2
APPLICATION NO. : 17/265663
DATED : June 18, 2024
INVENTOR(S) : Robert K. Schultz et al.

It is certified that error appears in the above-identified patent and that said Letters Patent is hereby corrected as shown below:

In the Specification

Column 11, Line 9 (approx.), delete "bioresorbable." and insert -- bioresorbable; --.

Column 21, Line 17 (approx.), delete "I2DTEtBu." and insert -- I2DTtBu. --.

Column 21, Lines 30-31, delete "alkenelene" and insert -- alkenylene --.

Column 26, Line 54, delete "trifluoracetic" and insert -- trifluoroacetic --.

Column 26, Line 54, delete "Trifluoracetic" and insert -- Trifluoroacetic --.

Column 28, Line 1, delete "hydroxybenzatriazole," and insert -- hydroxybenzotriazole, --.

Column 29, Line 19, delete "triethyleamine" and insert -- triethylamine --.

Column 35, Line 16 (approx.), delete "biocomapatibility" and insert -- biocompatibility --.

In the Claims

Column 57-58, Lines 35-40 (approx.), Claim 17, delete

"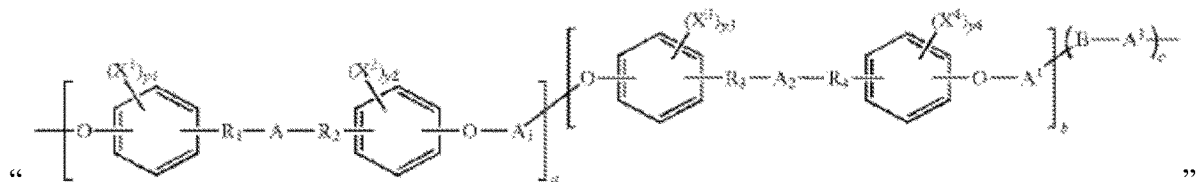"

and insert

Signed and Sealed this
Twenty-seventh Day of August, 2024

Katherine Kelly Vidal
*Director of the United States Patent and Trademark Office*